(12) United States Patent
Kirwan et al.

(10) Patent No.: US 8,968,405 B2
(45) Date of Patent: Mar. 3, 2015

(54) INTERBODY FUSION DEVICE AND METHOD OF OPERATION

(75) Inventors: John M. Kirwan, East Longmeadow, MA (US); R. Quinn Brown, East Longmeadow, MA (US); Hubert W. Pfabe, East Longmeadow, MA (US)

(73) Assignee: Incite Innovation LLC, Springfield, MA (US)

( * ) Notice: Subject to any disclaimer, the term of this patent is extended or adjusted under 35 U.S.C. 154(b) by 712 days.

(21) Appl. No.: 12/546,275

(22) Filed: Aug. 24, 2009

(65) Prior Publication Data
US 2010/0185289 A1 Jul. 22, 2010

Related U.S. Application Data

(60) Provisional application No. 61/145,787, filed on Jan. 20, 2009.

(51) Int. Cl.
| | | |
|---|---|---|
| A61F 2/44 | (2006.01) | |
| A61F 2/30 | (2006.01) | |
| A61F 2/46 | (2006.01) | |

(52) U.S. Cl.
CPC .............. *A61F 2/4455* (2013.01); *A61F 2/447* (2013.01); *A61F 2/4465* (2013.01); *A61F 2002/30405* (2013.01); *A61F 2002/30443* (2013.01); *A61F 2002/30504* (2013.01); *A61F 2002/30509* (2013.01); *A61F 2002/30576* (2013.01); *A61F 2002/30579* (2013.01); *A61F 2002/30904* (2013.01); *A61F 2002/4475* (2013.01); *A61F 2002/4627* (2013.01); *A61F 2002/4629* (2013.01); *A61F 2220/0025* (2013.01); *A61F 2220/0041* (2013.01); *A61F 2310/00023* (2013.01)
USPC ..................... 623/17.16; 623/17.11

(58) Field of Classification Search
USPC ........................................... 623/17.11–17.16
See application file for complete search history.

(56) References Cited

U.S. PATENT DOCUMENTS

| 4,904,261 | A | 2/1990 | Dove et al. |
|---|---|---|---|
| 4,955,908 | A | 9/1990 | Frey et al. |
| 5,397,364 | A | 3/1995 | Kozak et al. |
| 5,571,109 | A | 11/1996 | Bertagnoli |
| 5,800,547 | A | 9/1998 | Schafer et al. |

(Continued)

FOREIGN PATENT DOCUMENTS

| EP | 0697200 | 2/1996 |
|---|---|---|
| FR | 2835179 | 8/2003 |

(Continued)

OTHER PUBLICATIONS

International Search Report mailed Sep. 27, 2010 for PCT Application No. PCT/US2010/020969 filed Jan. 14, 2010.

(Continued)

*Primary Examiner* — Jerry Cumberledge
*Assistant Examiner* — Nicholas Plionis
(74) *Attorney, Agent, or Firm* — Cantor Colburn LLP

(57) ABSTRACT

An interbody fusion device is provided that includes an interbody cage, a fixation system and an actuation mechanism to deploy one or more blades. The cage acts as an intervertebral spacer and provides resistance to the compressive loads in the spinal column. The fixation system includes an anchor and a ramp. These components could be manufactured from various medical grade materials.

14 Claims, 39 Drawing Sheets

(56) References Cited

U.S. PATENT DOCUMENTS

| | | | |
|---|---|---|---|
| 5,800,550 A | 9/1998 | Sertich | |
| 5,888,223 A | 3/1999 | Bray, Jr. | |
| 5,976,139 A | 11/1999 | Bramlet | |
| 6,077,264 A | 6/2000 | Chemello | |
| 6,096,080 A | 8/2000 | Nicholson et al. | |
| 6,156,037 A | 12/2000 | LeHuec et al. | |
| 6,179,873 B1 | 1/2001 | Zientek | |
| 6,183,474 B1 | 2/2001 | Bramlet et al. | |
| 6,193,757 B1 * | 2/2001 | Foley et al. | 623/17.16 |
| 6,235,059 B1 | 5/2001 | Benezech et al. | |
| 6,241,769 B1 | 6/2001 | Nicholson et al. | |
| 6,432,106 B1 | 8/2002 | Fraser | |
| 6,443,954 B1 | 9/2002 | Bramlet et al. | |
| 6,447,546 B1 | 9/2002 | Bramlet et al. | |
| 6,461,359 B1 | 10/2002 | Tribus et al. | |
| 6,471,724 B2 | 10/2002 | Zdeblick et al. | |
| 6,558,423 B1 | 5/2003 | Michelson | |
| 6,579,290 B1 | 6/2003 | Hardcastle et al. | |
| 6,695,851 B2 | 2/2004 | Zdeblick et al. | |
| 6,716,245 B2 | 4/2004 | Pasquet et al. | |
| 6,743,256 B2 | 6/2004 | Mason | |
| 6,800,093 B2 | 10/2004 | Nicholson et al. | |
| 6,805,714 B2 | 10/2004 | Sutcliffe | |
| 6,890,355 B2 | 5/2005 | Michelson | |
| 6,972,019 B2 | 12/2005 | Michelson | |
| 6,984,234 B2 | 1/2006 | Bray | |
| 7,018,414 B2 | 3/2006 | Brau et al. | |
| 7,041,135 B2 | 5/2006 | Michelson | |
| 7,077,864 B2 | 7/2006 | Byrd, III et al. | |
| 7,135,024 B2 | 11/2006 | Cook et al. | |
| 7,163,560 B2 | 1/2007 | Mason | |
| 7,163,561 B2 | 1/2007 | Michelson | |
| 7,166,110 B2 | 1/2007 | Yundt | |
| 7,172,627 B2 | 2/2007 | Fiere et al. | |
| 7,232,464 B2 | 6/2007 | Mathieu et al. | |
| 7,291,170 B2 | 11/2007 | Huppert | |
| 7,297,162 B2 | 11/2007 | Mujwid | |
| 2003/0195514 A1 * | 10/2003 | Trieu et al. | 606/61 |
| 2003/0199983 A1 | 10/2003 | Michelson | |
| 2004/0249466 A1 | 12/2004 | Liu et al. | |
| 2005/0055027 A1 * | 3/2005 | Yeung et al. | 606/75 |
| 2006/0030851 A1 | 2/2006 | Bray et al. | |
| 2006/0173543 A1 | 8/2006 | Brau et al. | |
| 2006/0206208 A1 | 9/2006 | Michelson | |
| 2006/0241621 A1 | 10/2006 | Moskowitz et al. | |
| 2006/0253201 A1 | 11/2006 | McLuen | |
| 2007/0049943 A1 | 3/2007 | Moskowitz et al. | |
| 2007/0100452 A1 * | 5/2007 | Prosser | 623/17.11 |
| 2007/0106384 A1 | 5/2007 | Bray et al. | |
| 2007/0106388 A1 | 5/2007 | Michelson | |
| 2007/0233253 A1 | 10/2007 | Bray et al. | |
| 2007/0250167 A1 | 10/2007 | Bray et al. | |
| 2007/0276377 A1 | 11/2007 | Yundt | |
| 2008/0039846 A1 * | 2/2008 | Lee et al. | 606/63 |
| 2009/0105832 A1 | 4/2009 | Allain et al. | |
| 2009/0265007 A1 * | 10/2009 | Colleran | 623/17.16 |
| 2010/0016974 A1 * | 1/2010 | Janowski et al. | 623/17.16 |
| 2010/0185289 A1 | 7/2010 | Kirwan et al. | |
| 2011/0035007 A1 | 2/2011 | Patel et al. | |
| 2011/0230971 A1 | 9/2011 | Donner et al. | |
| 2012/0078371 A1 | 3/2012 | Gamache et al. | |

FOREIGN PATENT DOCUMENTS

| | | |
|---|---|---|
| WO | 9966867 | 12/1999 |
| WO | 2004080356 | 9/2004 |
| WO | 2008149223 A2 | 12/2008 |

OTHER PUBLICATIONS

Written Opinion of the International Searching Authority mailed Sep. 27, 2010 for Application PCT/US2010/020969 filed Jan. 14, 2010.

International Search Report mailed Mar. 25, 2013 for International Application Serial No. PCT/US2012/057764; International filed Sep. 28, 2012.

Written Opinion mailed Mar. 25, 2013 for International Application Serial No. PCT/US2012/057764; International filed Sep. 28, 2012.

Supplemental European Search Report for European Application No. EP 10 73 8901.7, date of completion of search dated Dec. 5, 2012.

* cited by examiner

INTERBODY FUSION DEVICE AND METHOD OF OPERATION

CROSS REFERENCE TO RELATED APPLICATIONS

The present application claims priority to U.S. Provisional Patent Application entitled "Interbody Fusion Device", Ser. No. 61/145,787 filed on Jan. 20, 2009, which is incorporated by reference herein in its entirety.

BACKGROUND OF THE INVENTION

The subject matter disclosed herein relates to an interbody fusion device, such as that used in lumbar or cervical spine procedures for example, and in particular relates to a stand-alone interbody fusion device having a self-contained fixation system.

Interbody fusion devices are common in spine procedures today. These devices encompass many products in the marketplace. Implants are constructed from PEEK, titanium and various other materials and have been designed for insertion through anterior, posterior and lateral approaches. Typically, interbody devices require additional fixation to create a fusion across the intended vertebral level. In lumbar surgery, this supplemental fixation can include an anterior plate or pedicle screws and rods inserted posteriorly in a 360° procedure. Studies have shown that interbody devices have poor outcomes when they are not combined with a method of fixation.

One type of interbody fusion device is called a stand-alone. This type of implant consists of an interbody device and a means of fixation all in one. Typically this fixation has been accomplished using screws that are placed through the implant and fixed at oblique angles to the adjacent superior and inferior vertebrae. This method requires considerable access due to the extreme angle of insertion for the screws.

While existing interbody fusion devices are suitable for their intended purposes, improvements may be made. In particular, it is desirable to have a stand-alone interbody fusion device with an integrated fixation system that may be readily implanted while reducing the access needed by a surgeon during a spinal procedure.

BRIEF DESCRIPTION OF THE INVENTION

In accordance with one embodiment of the invention, an interbody fusion device is provided having a cage. The cage includes a first contact surface and a second contact surface opposite the first contact surface. A ramp is coupled to the cage, the ramp includes a first surface thereon. A first anchor includes a body that is movably coupled within the cage, the first anchor has at least one blade extending from the body and an end adjacent the ramp. The at least one blade is arranged to cooperate with the first surface to direct the at least one blade from the first contact surface when the first anchor moves from the first position to the second position.

In accordance with another embodiment of the invention, an interbody fusion device for implanting between vertebrae is provided where the vertebrae have an anterior side and a posterior side. The interbody fusion device includes a cage having a first contact surface and a second contact surface. The cage also includes an anterior wall that is arranged between the first contact surface and the second contact surface. A ramp portion is arranged adjacent the anterior wall, and a first opening is arranged between the first contact surface and the second contact surface adjacent the ramp portion. An anchor is slidably coupled to the cage and includes at least one blade, wherein the anchor is movable between a first position towards the anterior wall to a second position, wherein the at least one blade cooperates with the ramp portion to move through the first opening when the anchor moves from the first position to the second position.

In accordance with another embodiment of the invention, an interbody fusion device is provided having a cage. The cage includes a pair of opposing contact surfaces and a wall on one end arranged between the contact surfaces. The cage further includes a center portion disposed adjacent the wall. The cage also includes a first opening extending through the contact surfaces between the center portion and the wall, a second opening arranged in the wall, and a third opening is arranged in the center portion. An anchor is slidably arranged in the third opening, the anchor has a body and at least one blade. The body is movable between a first position, within the cage, to a second position where the at least one blade extends through the first opening.

In accordance with one embodiment of the invention, a method of fusing adjacent vertebrae is provided where the vertebrae have an anterior side and a posterior side. The method includes the step of providing an interbody fusion device that includes a cage and an anchor with at least one blade. A surgical tool is coupled to the anchor. The interbody fusion device is inserted between the vertebrae. The surgical tool is actuated to translate the anchor from a first position to a second position with the at least one blade extending into at least one of the vertebrae.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed descriptions taken in conjunction with the accompanying drawings in which:

The detailed description explains embodiments of the invention, together with advantages and features, by way of example with reference to the drawings.

DETAILED DESCRIPTION OF THE INVENTION

Figure 112:
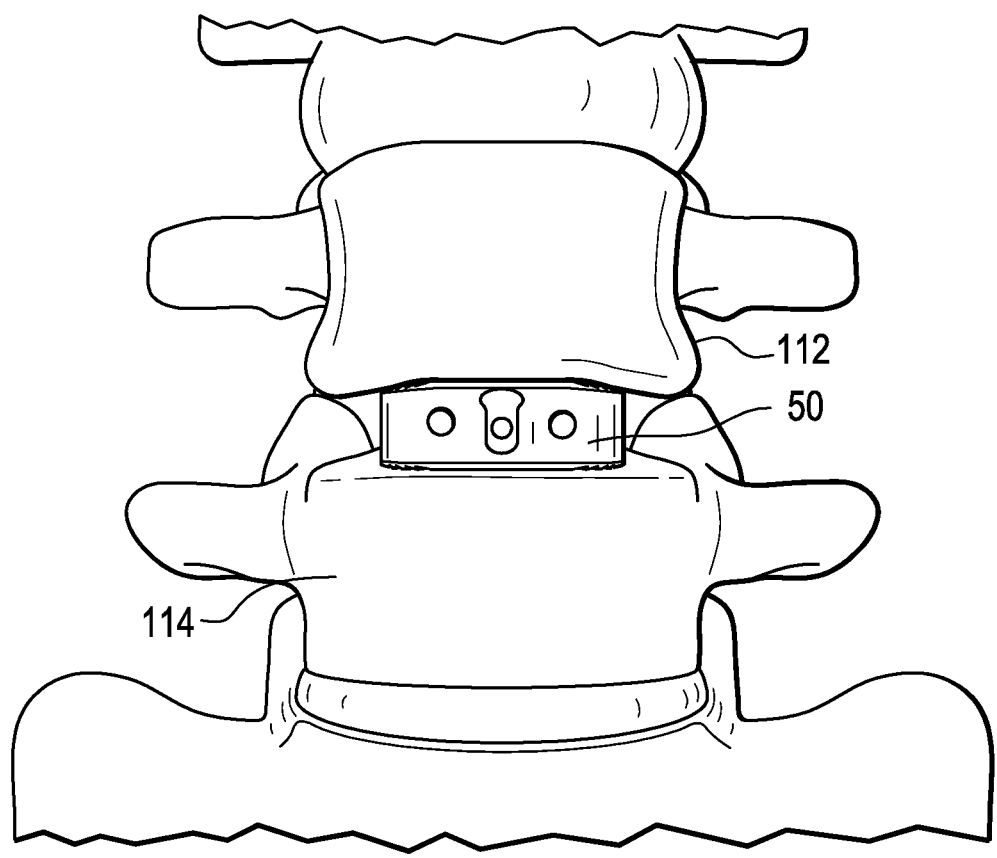
FIG. 112 is a front plan view illustration of an exemplary interbody fusion device of FIG. 14 inserted between vertebrae.
Figure 113:
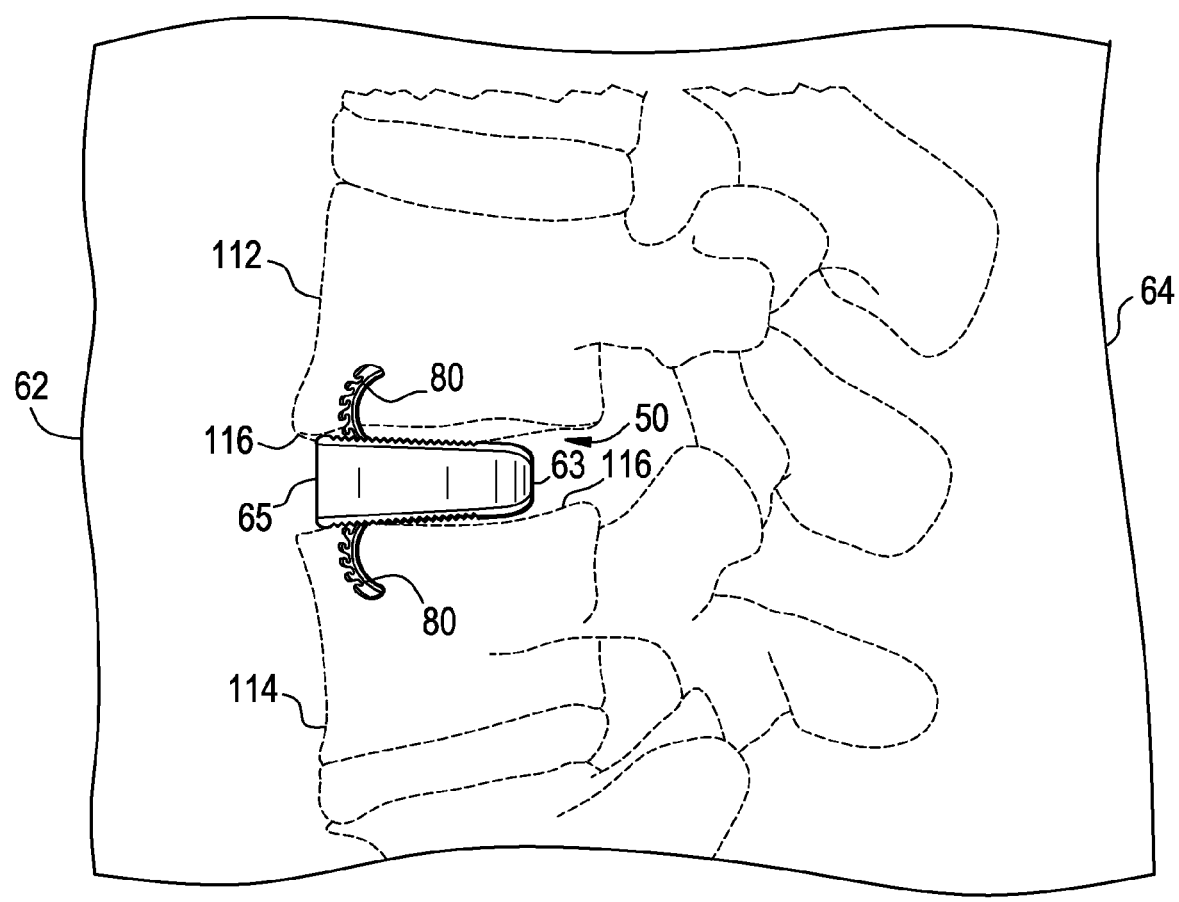
FIG. 113 is an side plan view illustration the superior vertebrae and the inferior vertebrae illustrated in phantom line of the exemplary interbody fusion device of FIG. 106; and, FIG. 114 is a front plan view illustration with the superior vertebrae and the inferior vertebrae illustrated in phantom line of the exemplary interbody fusion device of FIG. 106.
Figure 114:
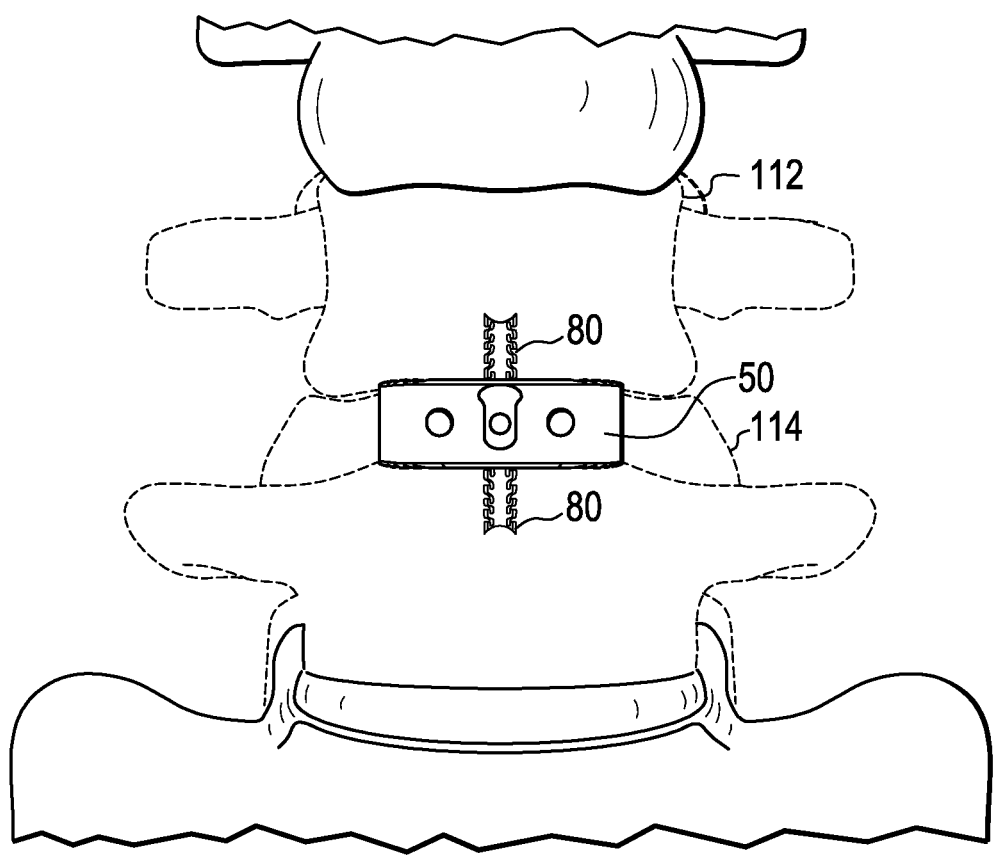

Referring to FIGS. 1-13, an exemplary interbody fusion device 50 having an interbody cage 52 and a fixation device 54 is illustrated. The interbody cage 52 can be used alone with supplemental fixation, such as rods and screws or a plate for example, or with the included fixation device 54, thereby providing a stand-alone design. The interbody cage 52, can be constructed of various biocompatible materials including, but not limited to, titanium or a polymer such as polyetheretherketone (PEEK) for example. With the fixation device 54 in place, the interbody fusion device 50 would be placed between the adjacent vertebrae after the partial or complete disc removal as illustrated in FIGS. 112-114. Once in place, the fixation device 54 would be actuated through a screw member 56. This action would deploy the anchor 58 or anchors into the adjacent superior and inferior vertebral bodies 112, 114 (FIG. 112), thereby fixing the implant in place. Thus the interbody fusion device 50 provides advantages in that supplemental fixation, such as pedicle screws and rods or an anterior plate for example, and its associated increased surgical time, is obviated. Further, the interbody cage 52 may include an optional opening 60 that may be used for autograft or alternative biomaterials to facilitate bone in-growth. The surgeon may utilize a tool or tools to facilitate the insertion of the interbody fusion device 50, in conjunction with features 75 for example, to both place the interbody fusion device 50 and provide a means for actuation of the screw member 56 to deploy the fixation device 54.

It should be appreciated that while the interbody cage 52 is illustrated with the opening 60, this is for exemplary purposes and the claimed invention should not be so limited. For example, in different applications, it may be desirable to have the interbody cage 52 be substantially solid for example. While the exemplary embodiment discusses the spinal procedures with respect to an anterior insertion approach, the claimed invention may also be used in other spinal procedures, such as but not limited to posterior insertion and lateral insertion for example.

As used herein the term "anterior" refers to the front side from the perspective of the patient, while the term "posterior" refers the backside from the perspective of the patient. Further, as used herein, the term "superior" means closer to the head of the patient and "inferior" means closer to the feet of the patient.

The interbody cage 52 is a generally oblong shaped member sized to tightly fit between vertebrae. The interbody cage 52 tapers from the anterior side 62 to the posterior side 64 to match patient anatomy. In the exemplary embodiment, the top contact surface 66 and bottom contact surface 68 include a plurality of optional teeth or grooves 70 that engage the adjacent superior and inferior vertebrae to assist in maintaining the interbody fusion device 50 in place.

It should be appreciated that the taper, or angle between the contact surfaces 66, 68 may be varied to match the patient anatomy. The height, or distance between the contact surfaces 66, 68 may also be changed to match the patient anatomy. Further, while the contact surfaces 66, 68 are illustrated as being substantially flat and tapered, other profiles may be used, including but not limited to parallel surfaces or convex surfaces for example. Additionally, the interbody cage 52 may be cylindrical, such as that shown in U.S. Pat. No. 5,782, 919, which is incorporated by reference in its entirety.

Figure 5:
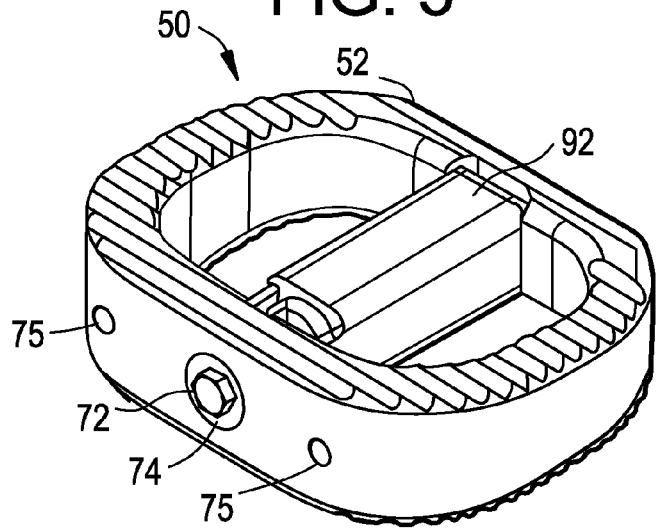
FIGS. 5-6 are an illustration of an interbody fusion device of FIG. 1 with another embodiment cage and screw member.
Figure 6:
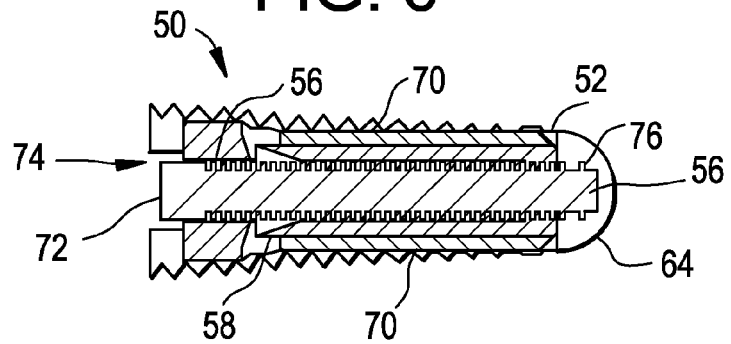
Figure 7:
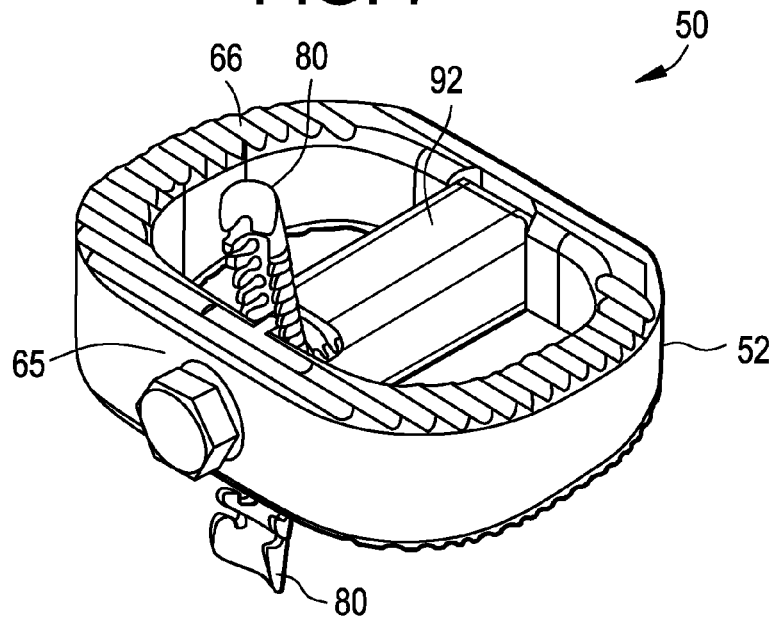
FIGS. 7-10 are an illustration of an interbody fusion device of FIG. 1 in the extended or deployed position.

In the embodiments illustrated in FIG. 1-13, the interbody cage 52 includes an opening sized to receive the screw member 56. The screw member 56 includes an actuation portion 72 that is configured to interact with a tool to allow the surgeon to rotate the screw member 56 after implanting the interbody fusion device 50 between the desired vertebrae. In one embodiment, the actuation portion 72 may be a hexagonal head that extends from the interbody cage 52, such as that shown in FIGS. 1-4 for example. Alternatively, the actuation portion 72 may rest within an opening 74 such that the actuation portion 72 is contained within the interbody cage 52, such as is shown in FIGS. 5-6 for example. In one embodiment, the opening in interbody cage 52 for the screw member 56 extends through the interbody cage 52 as shown in FIG. 6. In this embodiment, the screw member 56 is captured in the interbody cage 52 by a retaining member or feature, such as a snap ring 76 for example. Alternatively, the retaining member may be adjacent the actuation portion 72.

It should be appreciated that in those embodiments where the insertion access point is not anterior, the location of the actuation portion 72 may be changed. In general, the position of the actuation portion 72 will be such that the actuation portion 72 will be oriented toward the surgeon's access point.

The interbody cage 52 also includes a pair of slots 71, 73 adjacent and centrally located within the opening 60. The anterior slot 71 captures a ramp member 94 while the posterior slot 73 captures a guide housing 92. The guide housing 92 also includes a body portion 96 (FIG. 104-107), which when inserted into the interbody cage 52 as illustrated in the exemplary embodiment, substantially bifurcates the opening 60 to define the graft/biomaterial packing space. Pairs of projections 98 extend from the guide housing 92 and engage the ramp member 94. The guide housing 92 also includes a center bore 95 that is sized to receive the screw member 56. As will be discussed in more detail below, the center bore 95 may include one or more features 90 that are arranged to cooperate with features on the anchor 58, which is slidably arranged in the center bore 95. The body portion 96 also provides additional advantages with embodiments using a screw member 56 by covering the thread portion of the screw member 56 and inhibiting the migration of graft/biomaterial into the threads. It should be appreciated that in embodiments having a substantially solid interbody cage 52, the body portion 96 may be altered since the threads will not need to be shielded from the graft/biomaterial.

Figure 97:
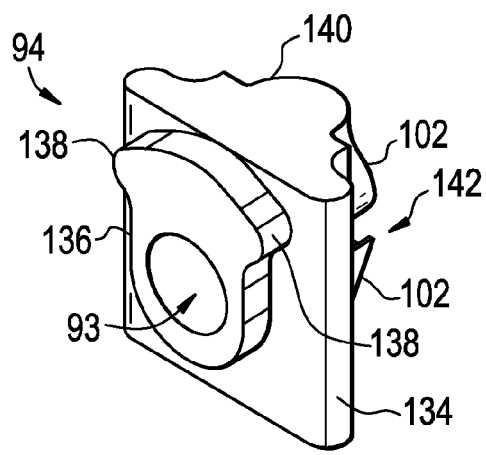
FIGS. 97-100 illustrate another embodiment of a ramp member for use with the interbody fusion device of FIGS. 14-19, 28-29.
Figure 98:
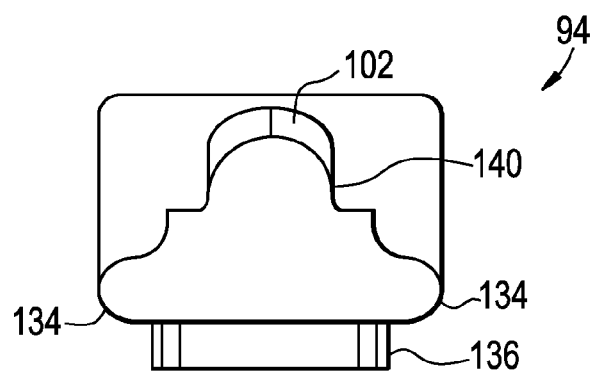
Figure 99:
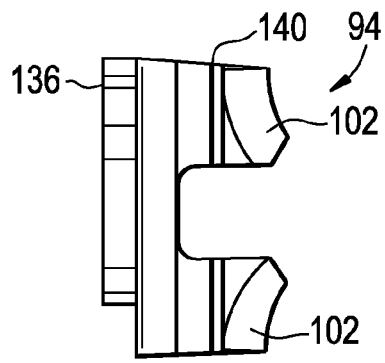
Figure 100:
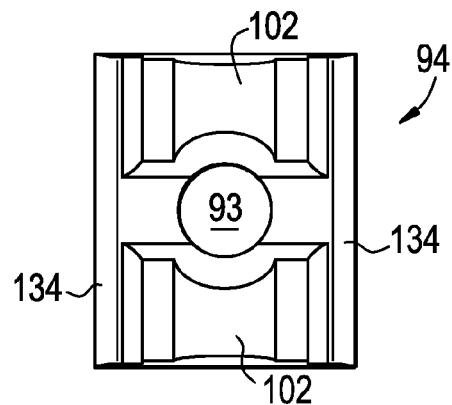

Referring now to FIGS. 14-19, another embodiment of the interbody fusion device 50 is shown. This embodiment is similar to the embodiment of FIGS. 1-13 including a interbody cage 52 having contact surfaces 66, 68. An anterior wall 65 includes slot 71 to capture a ramp member 94, such as the ramp member 94 embodiment shown in FIG. 97 for example. As will be discussed in more detail below, in one embodiment the ramp member 94 and the slot 71 include features that cooperate to allow the ramp member 94 to be attached to the interbody cage 52 by a snap-fit coupling.

The anterior wall further includes a pair of features 75, such as a threaded hole for example, to facilitate the attachment of an insertion tool as discussed in more detail below. The interbody cage 52 further includes a center portion 67 that provides the functionality of the guide housing 92 discussed above. In one embodiment, the center portion 67 bifurcates the interbody cage 52 to define the openings 60 to allow the insertion of graft/biomaterial. The center portion 67 extends from the posterior wall 63 towards the ramp member 94. Pair of arms 77 project from the center portion 67 to connect the center portion 67 to the anterior wall 65. A wall 81 is arranged on the end of the center portion 67, separating the arms 77. As with the guide housing 92, an opening or center bore 95 is formed in the center portion 67 through wall 81. Slidably arranged within the center bore 95 is the anchor 58. The center bore 95 may include features 90 to orient the anchor 58 in the center bore 95. The center bore 95 is arranged in the center portion 67 to be substantially co-axial with an opening 93 in the ramp member 94.

Figure 31:
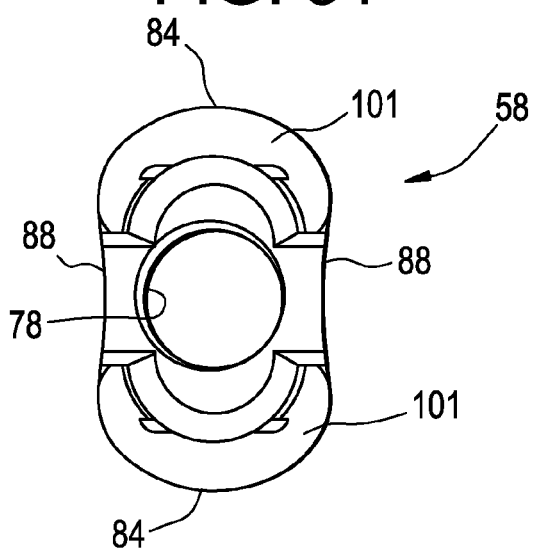
Figure 32:
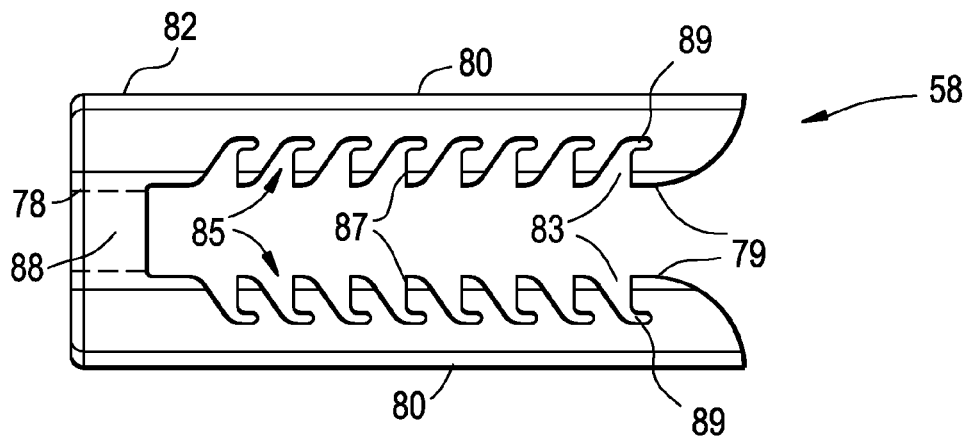
Figure 33:
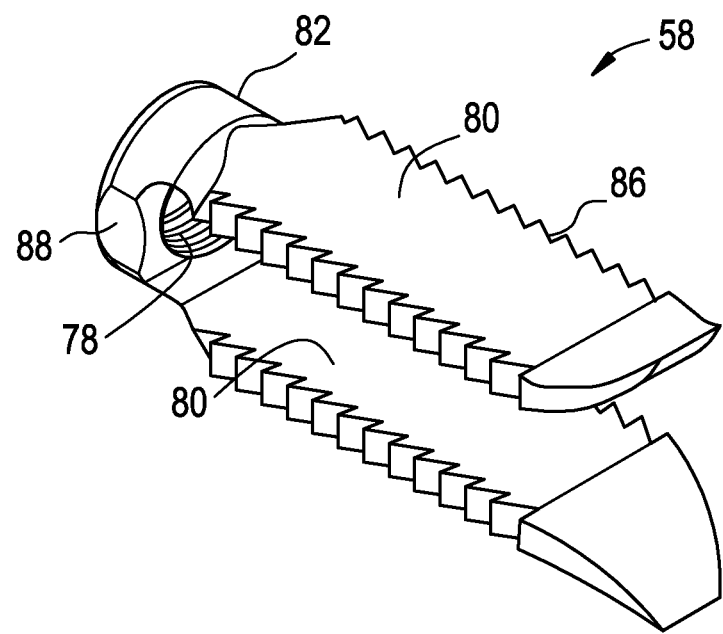
FIGS. 33-37 are an illustration of another embodiment of an anchor for use in the interbody fusion device shown in FIGS. 1-29.
Figure 34:
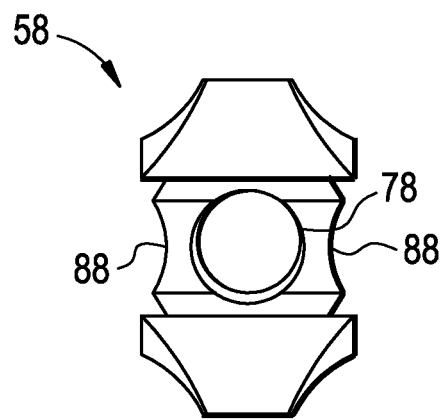

The embodiment of FIGS. 14-19 does not include a screw member 56. Instead, the interbody fusion device 50 cooperates with a surgical tool 170, such as the one illustrated in FIGS. 108-111 for example. The surgical tool includes a shaft 171 having a capturing portion, such as a threaded end 172 for example, that is sized to be received in the opening 93 of ramp member 94. In this embodiment, the threaded end 172 is further adapted to couple to the threaded portion 78 of the anchor 58 (see for example FIGS. 30-32). As will be discussed in more detail below, after the threaded end 172 is coupled to the anchor 58, the surgical tool 170 is actuated, such as by rotating a actuation knob 186 for example, causing the shaft 171 to move axially within the surgical tool 170. Since the surgical tool 170 is firmly coupled to the interbody cage 52, this results in the axial movement of the anchor 58 towards the ramp member 94. As the surgical tool 170 continues to be actuated, the blade 80 will contact the ramp member and deflect through the openings 91 in the contact surfaces 66, 68. While the threaded end 172 is illustrated, this is for exemplary purposes, and other capturing portions or geometries may be used.

Figure 19:
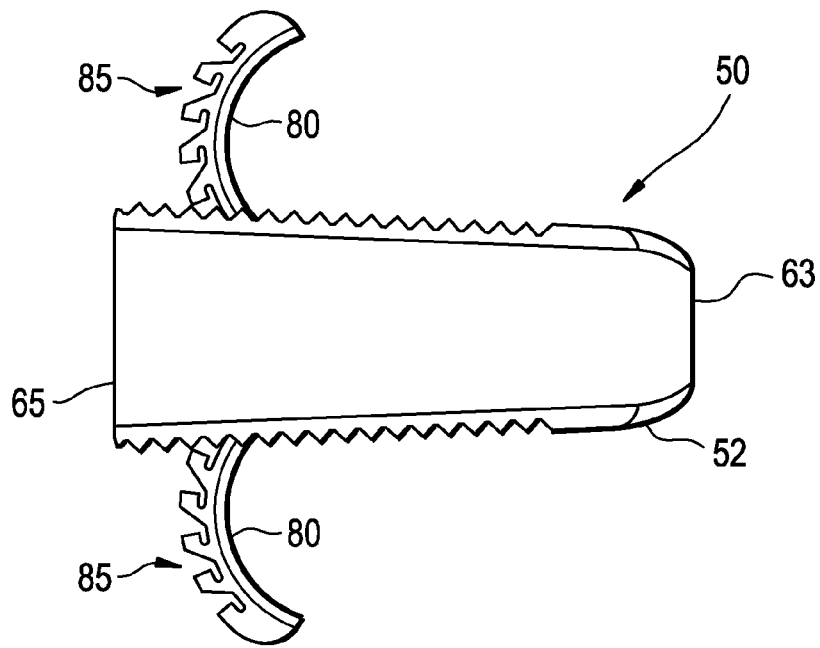
Figure 20:
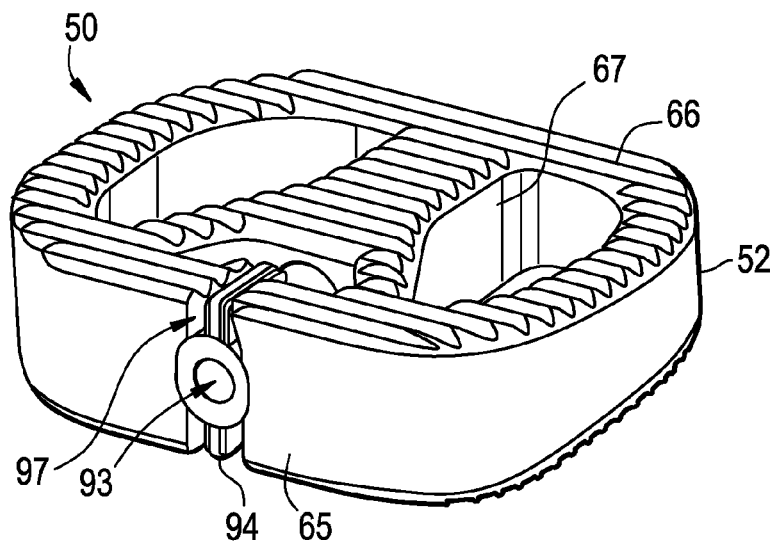
FIGS. 20-22 are an illustration of an interbody fusion device in accordance with another embodiment of the invention.
Figure 21:
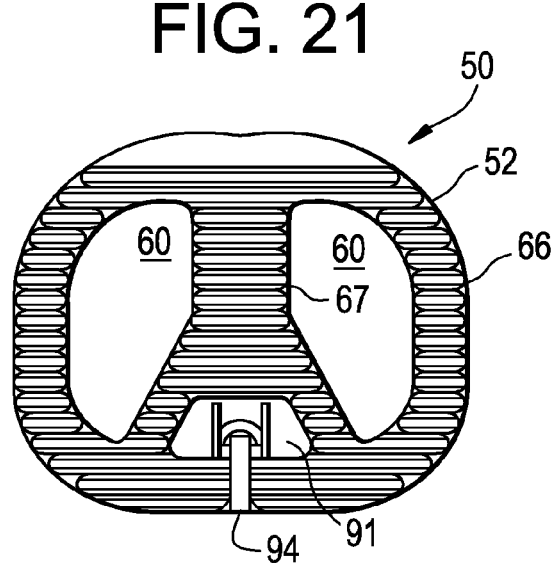
Figure 22:
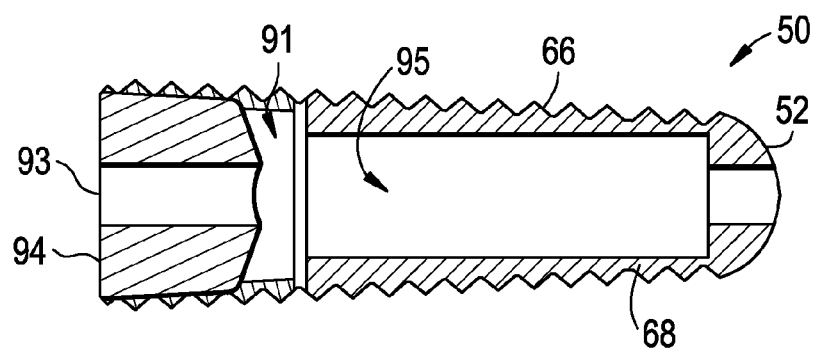
Figure 94:
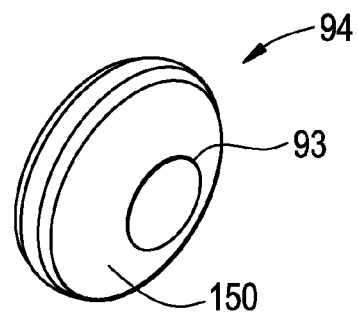

Another embodiment of interbody fusion device 50 is illustrated in FIGS. 20-22. This embodiment is similar to the embodiment of FIG. 14-19 wherein the interbody cage 52 includes contact surfaces 66,68 and a center portion 67 that bifurcates the interbody cage 52 to define openings 60. In this embodiment, the anterior wall 65 includes a slot 97 that divides the anterior wall 65 into two sections. The slot 97 is sized to receive a ramp member 94, such as the ramp member 94 illustrated in FIG. 94 for example. In this embodiment, the ramp member 94 is inserted axially into the slot 97 rather than transversely through one of the contact surfaces 66, 68. The ramp member 94 includes an opening 93 that is arranged co-axially with the center bore 95 of the center portion 67. The anchor 58 is slideably arranged in the center bore 95. The opening 93 is sized to receive the shaft 171 to allow the anchor 58 to be deployed from the retracted position to the extended position with the blade 80 extending through the opening 91 as discussed above.

Figure 23:
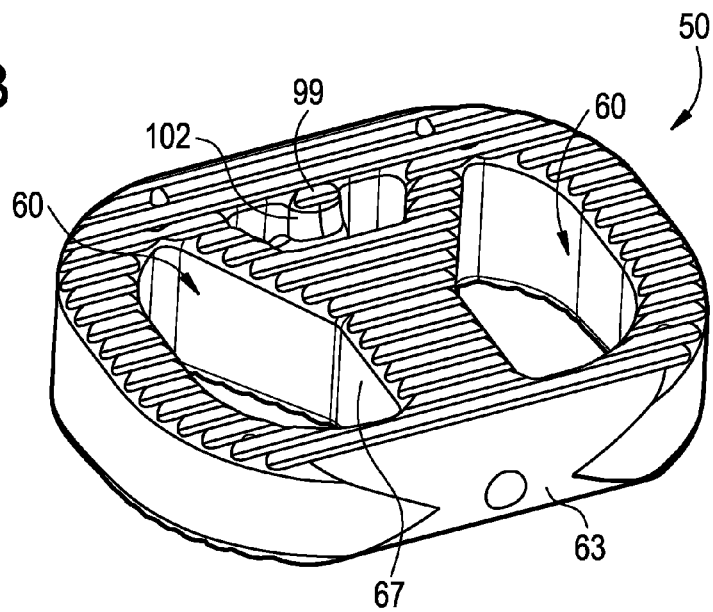
FIGS. 23-25 are an illustration of another interbody fusion device in accordance with another embodiment of the invention.
Figure 24:
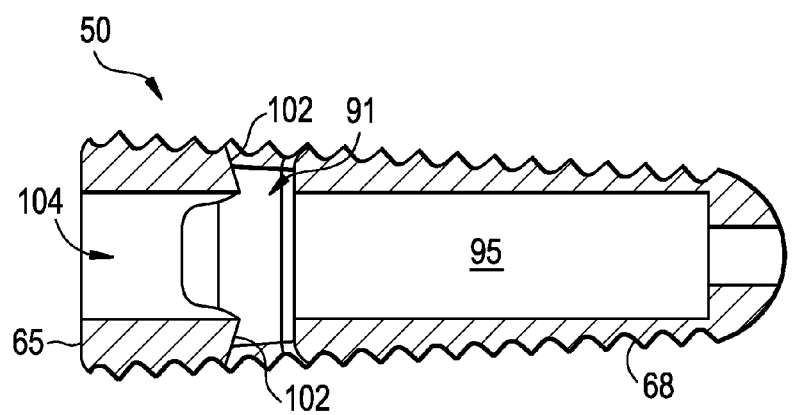
Figure 25:
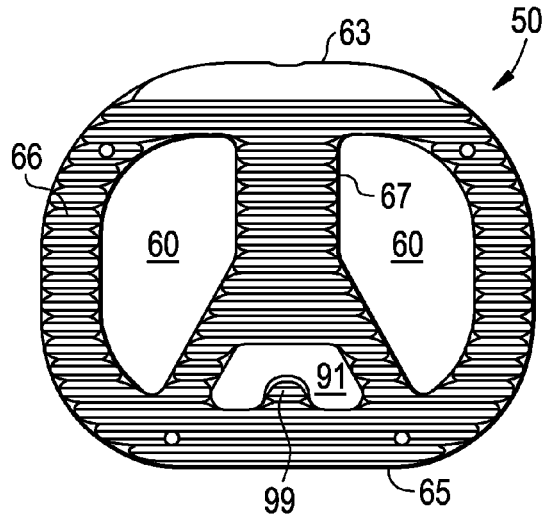

Another embodiment of the interbody fusion device 50 is illustrated in FIGS. 23-25. This embodiment is similar to the embodiment of FIG. 14-19 where the interbody cage 52 includes contact surfaces 66, 68 and a center portion 67 that bifurcates the interbody cage 52 to define openings 60. In this embodiment, the ramp member 94 is integrated into the interbody cage 52, wherein the anterior wall 65 includes a projection 99 that extends into the opening 91. The projection 99 includes a ramp surface 102 that deflects the blade 80 through the opening 91 as the anchor 58 is moved from the first or retracted position to a second or extended position. The anterior wall 65 includes an opening 104 that is arranged co-axial with the center bore 95.

Since the interbody fusion device 50 illustrated in FIGS. 23-25 does not have a separate ramp member 94, the opening 104 needs to be sized to be larger to allow the anchor 58 to be installed. In order for the anchor 58 to engage the ramp surface 102, the anchor 58 may have a flared piercing portion 84, such as the anchor illustrated in FIG. 33-37, 44-54, or 62-63, whereby the flared end is compressed as the anchor 58 is inserted. Once the anchor 58 is installed and the flared end released, the flared end would be arranged in the opening 91. In another embodiment, the anchor 58 is installed through the opening 104 and a tool is used to deform the anchor piercing portion 84 to bend up into the opening 91. In other embodiments, the center portion 67 may include an additional opening or slot (not shown) that allows the insertion of the anchor 58 from either the top contact surface 66, the bottom contact surface 68 or through the side wall.

Figure 26:
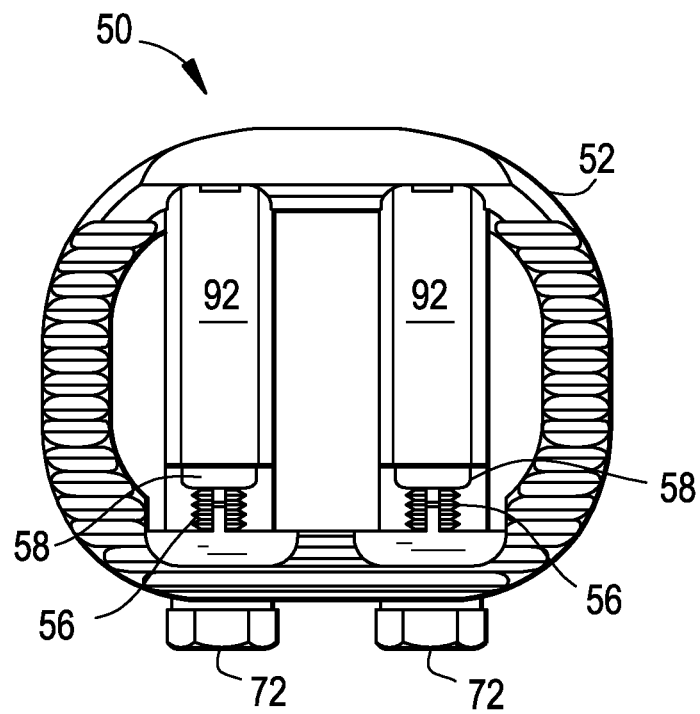
FIG. 26-27 are an illustration of an interbody fusion device having multiple screw members and anchors in accordance with another embodiment of the invention.
Figure 27:
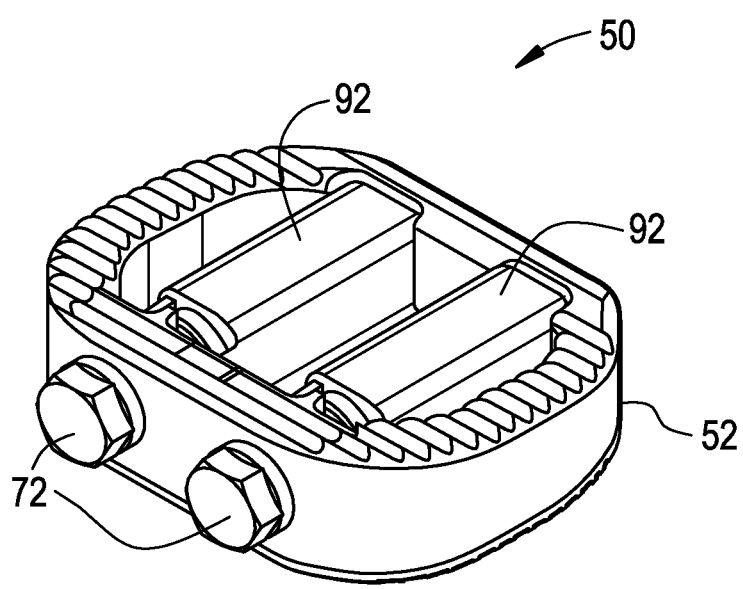

In some embodiments, the interbody fusion device 50 may include multiple anchors 58 as shown in FIGS. 26-27. In this embodiment, there may be two or more screw members 56 each having an actuation portion 72, coupled to the interbody cage 52. Each screw member 56 has an anchor 58 (or anchor 154) coupled within a guide housing 92. In other embodiments (not shown), there may only be a single actuation portion 72 that drives both anchors 58 during deployment. It should be appreciated that the embodiment of FIGS. 26-27 may also be configured without the screw member 56 with the anchor being deployed in a similar manner to that described in the embodiments of FIGS. 14-25.

Figure 28:
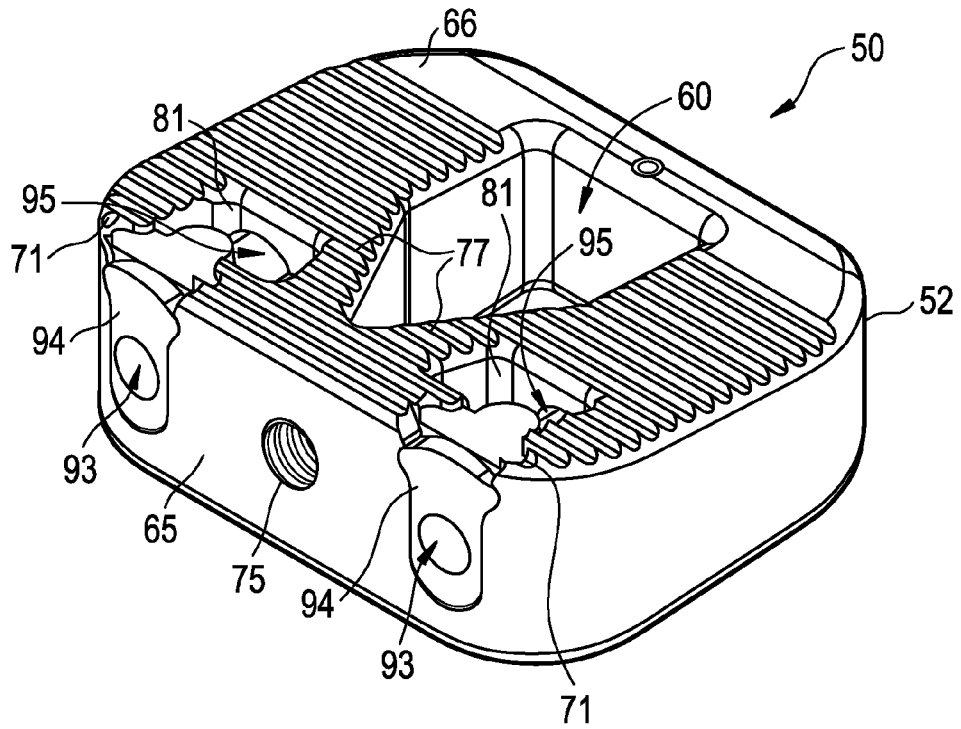
FIG. 28 is a perspective view illustration of an interbody fusion device having multiple anchors in accordance with another embodiment of the invention.
Figure 29:
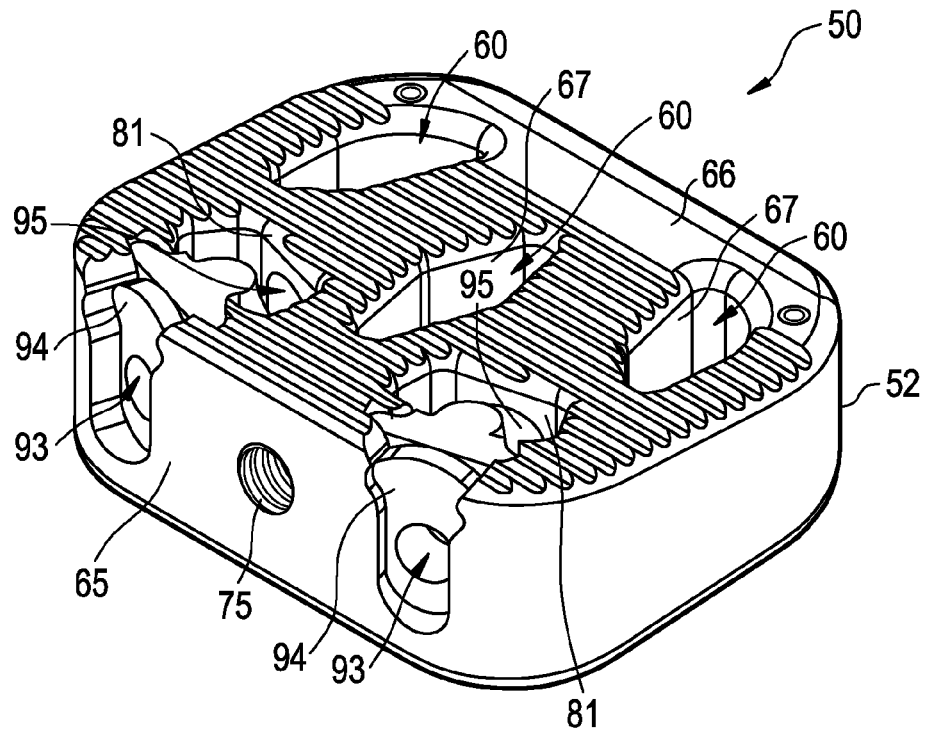
FIG. 29 is a perspective view illustration of an interbody fusion device having multiple anchors arranged on an angle in accordance with another embodiment of the invention.

Another embodiment of an interbody fusion device 50 having multiple anchors is illustrated in FIGS. 28-29. In the embodiment of FIG. 28, the anchors 58 are arranged substantially perpendicular to the anterior wall 65. In the embodiment of FIG. 29, the anchors 58 are arranged on an angle relative to the anterior wall 65. These embodiments include an interbody cage 52 having contact surfaces 66, 68. The anterior wall 65 includes a pair of slots 71, each of which captures a ramp member 94, such as the ramp member 94 shown in FIG. 97 for example. The ramp member 94 and the slot 71 cooperate to allow the ramp member 94 to be attached to the interbody cage 52 by a snap fit coupling. Each ramp member 94 includes an opening 93 that is arranged substantially co-axial with the opening 95 in the interbody cage 52.

The anterior wall 65 includes a feature 75, such as a threaded hole for example, to facilitate the attachment of an insertion tool as discussed in more detail below. In one embodiment, the feature 75 is centered on the anterior wall 65 between the slots 71. An opening 60 is arranged centrally in the interbody cage 52 that extends through the contact surfaces 66, 68 to allow the insertion of graft/biomaterial. Arms 71 are arranged between the opening 60 to define a second opening 91 adjacent the each ramp member 94 in a similar manner to that described above with respect to the embodiment of FIGS. 14-19. In the embodiment of FIG. 29, two additional openings 60 to allow insertion of graft/biomaterial are provided adjacent center portion 67.

As discussed above in reference to the embodiment of FIGS. 14-19, a surgical tool, such as surgical tool 170 for example, is coupled to the interbody fusion device 50 via feature 75 and the anchors 58 via the openings 93. The surgical tool is arranged to move the anchors 58 within the opening 95 between the first retracted position to a second extended position. The surgical tool may have a single shaft and capturing portion as illustrated in FIGS. 108-111, or may have multiple shafts (not shown) that may individually or simultaneously deploy the anchors.

It should also be appreciated that in embodiments where the height of the interbody cage 52 is increased, the outside profile of the guide housing 92, such as the height of the body portion 96 for example, will also increase in proportion to the interbody cage 52. In some embodiments, the anchor 58 may increase in height, or have longer blade 80. The interbody fusion device 50 may include additional features, such as a locking mechanism or member that prevents movement of the anchor 58 after it is deployed by the surgeon. The locking member may take several forms, including but not limited to a setscrew or a cap (not shown) that engages the actuation portion 72 of screw member 56, such as in opening 74 for example.

It should also be appreciated that while the embodiments herein illustrate the guide housing 92 and the center portion 67 as extending substantially normal to the anterior side 62 and posterior side 64, this is for exemplary purposes and the claimed invention should not be so limited. In other embodiment, such as those used in procedures using a lateral insertion of the interbody fusion device 50 for example, the guide-housing 92/center portion 67 may be oriented on an angle relative to the anterior side 62 and posterior side 64. In one embodiment, the guide-housing 92/center portion 67 is arranged substantially parallel to the anterior wall 65 and the posterior wall 63.

It should further be appreciated that while the embodiments disclosed herein refer to the screw member 56 actuation portion 72 or the surgical tool 170 as being arranged on the anterior side 62, this is for exemplary purposes and the claimed invention should not be so limited. In some embodiments, such as those used in procedures using posterior insertion of the interbody fusion device 50 for example, the screw member 56 actuation portion 72 or the surgical tool 170 may be accessed from the posterior side 64 or another lateral position. It should also be appreciated that in some embodiments, the anchor 58 may be actuated from a lateral or posterior position.

Figure 30:
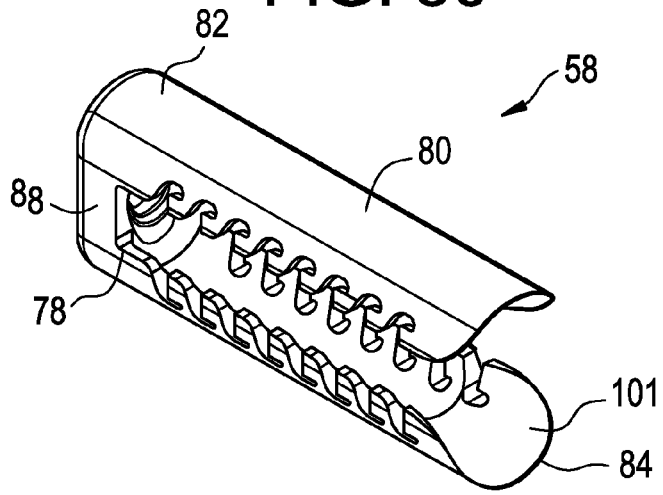
FIGS. 30-32 are an illustration of an exemplary anchor for use in the interbody fusion device shown in FIGS. 1-29.
Figure 82:
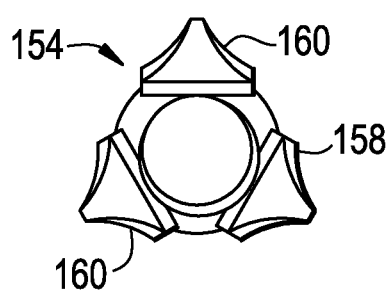
Figure 83:
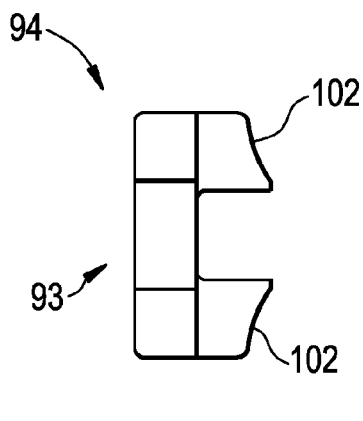
FIGS. 83-84 are an illustration of an embodiment of a ramp member used in the interbody fusion device of FIGS. 1-19.
Figure 84:
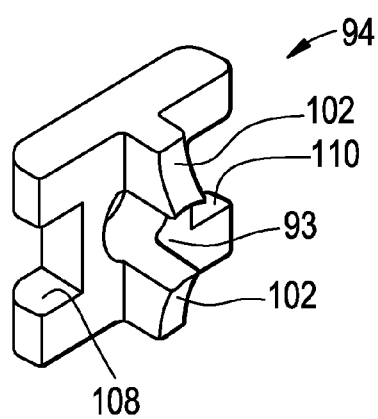
Figure 85:
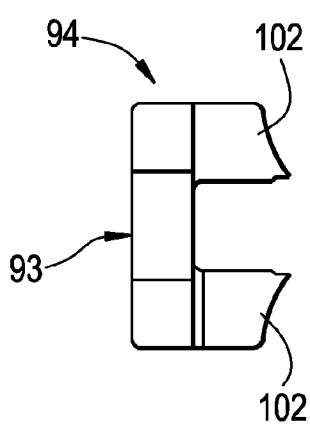
FIGS. 85-86 are an illustration of another embodiment of a ramp member used in the interbody fusion device of FIGS. 1-19.
Figure 86:
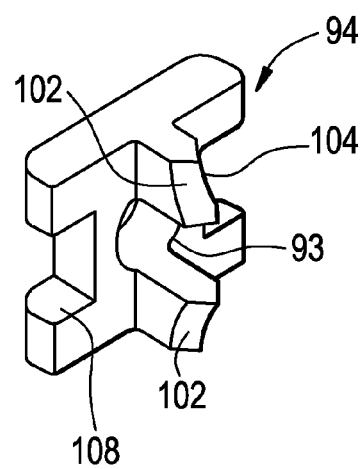
Figure 87:
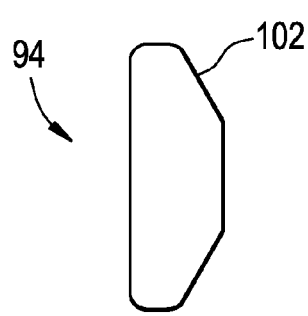
FIG. 87-88 are an illustration of another embodiment of a ramp member for use with the interbody fusion device shown in FIGS. 1-19.
Figure 88:
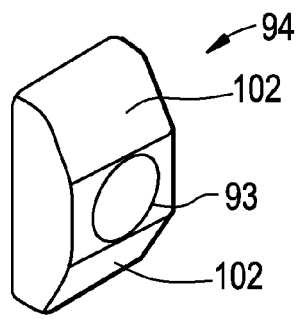
Figure 89:
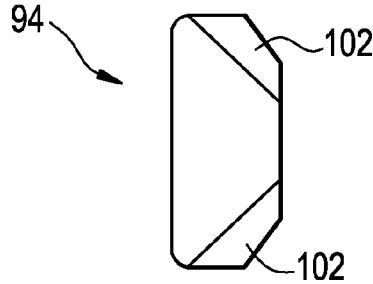
FIGS. 89-90 are an illustration of another embodiment of a ramp member used with in the interbody fusion device of FIGS. 1-19.
Figure 90:
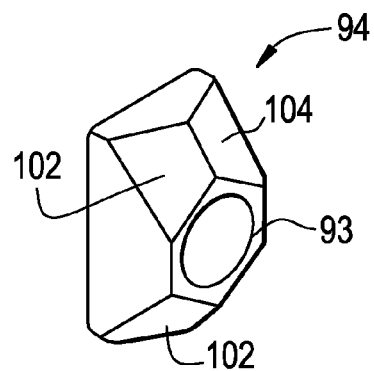
Figure 91:
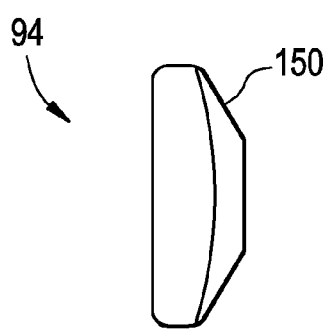
FIGS. 91-92 are an illustration of another embodiment of a conical ramp member for use with the interbody fusion device shown in FIGS. 1-19.
Figure 92:
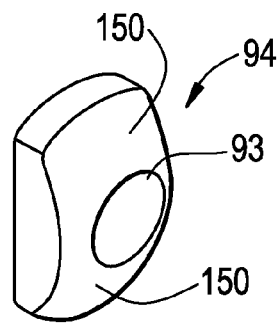
Figure 93:
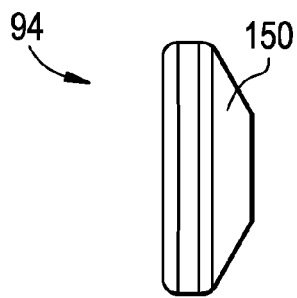
FIGS. 93-94 are an illustration of another embodiment of a conical ramp member for use with the interbody fusion device shown in FIGS. 1-19.

As discussed above, the anchor 58 is slidably retained in the center bore 95. The anchor is movable in the center bore 95 whereby the anchor 58 is slid toward the ramp member 94 from a retracted or first position, shown in FIGS. 2, 6 and 17 for example, to an extended or second position, shown in FIGS. 8, 12 and 19 for example, where the blade member extends through the opening 91. In some embodiments, such as those illustrated in FIGS. 1-13 for example, the screw member 56 moves the anchor 58. In other embodiments, such as those illustrated in FIGS. 14-25 for example, the surgical tool 170 moves the anchor 58. It should be appreciated that the anchor 58 may include a number of different features, as shown in FIGS. 30-82 for example. Some of these features include, but are not limited to an anchor having: two blades; four blades (FIGS. 41-43, 47-54); blades with slots (FIGS. 30-32, 38-43, 57-61, 62-65 and 68-69); blades with teeth (FIGS. 33-37, 44-49, 50-54 and 68-69); blades with teeth and slots; flat bladed anchors (FIGS. 33-37, 44-49 and 50-54); and curved anchors (FIGS. 30-31, 38-43, 55-56, 57-61, and 62-69) or a combination of the foregoing for example.

Figure 35:
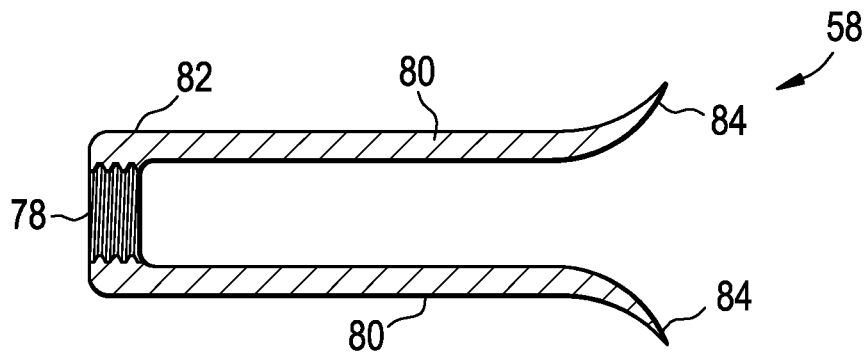
Figure 36:
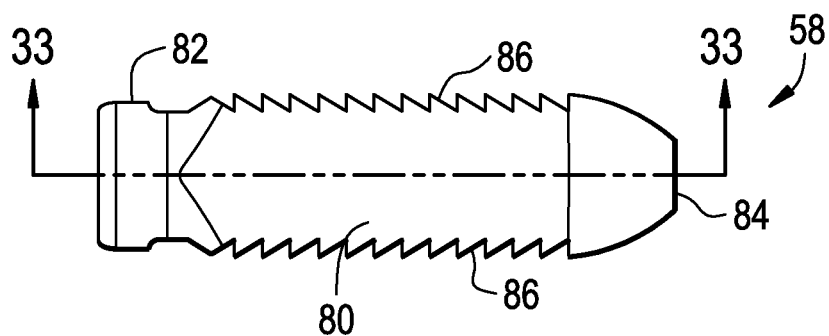
Figure 37:
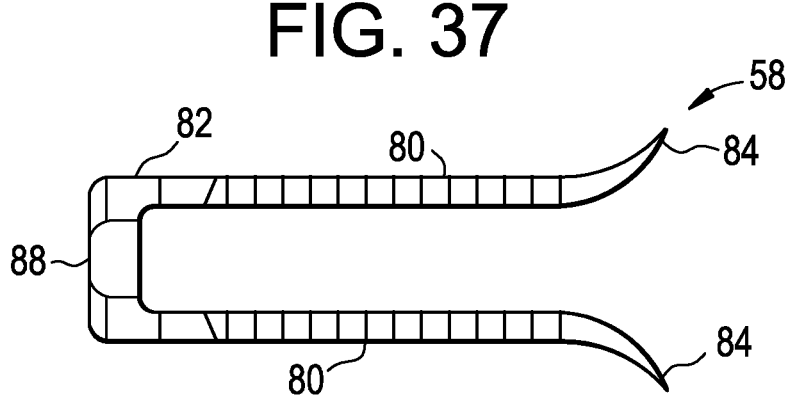
Figure 38:
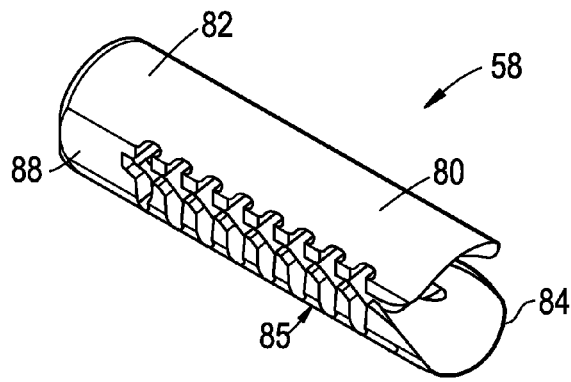
FIGS. 38-40 are an illustration of another embodiment of an anchor for use in the interbody fusion device shown in FIGS. 1-29.
Figure 39:
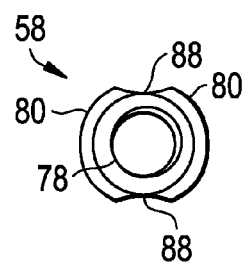
Figure 40:
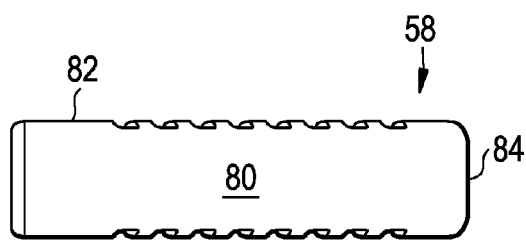

The anchor 58 includes a body 82 with threaded portion 78 that engages the screw member 56 or the shaft 171. One or more blades 80 extend from the body 82 and extend substantially parallel to the center bore 95. Opposite the body 82, each blade 80 includes a piercing portion 84. The piercing portion 84 may be flat as shown in FIG. 30, or flared/curved as shown in FIG. 35 for example. The piercing portion 84 may further include a tapered region 101. In embodiments having multiple blades 80, a slot 105 may be arranged between adjoining blades, such as is shown in FIGS. 41-43 and FIGS. 47-49 for example. The slot 105 may extend substantially the entire length of the blade 80, or alternatively may be shorter in length, such as extending to the midpoint of the blade 80 for example. The teeth 86 may extend in a plane parallel to the blade 80, as shown in FIG. 36, or the blade 80 may be curved and the teeth 86 conforming to the shape of the blade 80.

In the exemplary embodiments, such as that shown in FIGS. 30-32 and 57-61 for example, the blade 80 includes slots 85 that extend from an edge 79 of the blade 80. The slots 85 include a curved portion 83, surface 87, and a relief area 89. The curved portion 83 removes material from the blade 80 that may facilitate the bending of the blade 80 during deployment. Similarly, the relief area 89 facilitates bending and also reduces the stress in the blade 80, lowering the potential for stress fractures. This embodiment may provide further advantages in that the surface 87 may provide further resistance to withdrawal of the blade 80 from the vertebrae.

In the exemplary embodiment, the anchor 58 may also include one or more features 88 on the body 82. The features 88 may be an inward cylindrical shape as illustrated in FIG. 30, or may have other profiles such as but not limited to an outward cylindrical shape and a flat surface for example. The feature 88 may be shaped to match an adjacent feature 90 on the guide housing 92 or the center portion 67. The features 88, 90 cooperate to maintain the anchor 58 properly oriented during assembly and while the blades 80 are being deployed during a spinal procedure. It should be appreciated that the features 88, 90 may take other forms that allow the anchor 58 properly oriented, such as a pin and a slot for example.

In the exemplary embodiment, the anchor 58 is made from a material, such as titanium for example, that may be defined by a stress-strain curve having an elastic range and a plastic range. As used herein, this means that if the stress on the material does not exceed the materials elastic limit, the article may be repeatedly deformed and the article will return to its original shape. Once the elastic limit is exceeded, the material plastically deforms and the article does not return to its original shape. In the exemplary embodiment, the blade 80 is arranged to plastically deform as anchor 58 is moved from the retracted or first position to the extended or second position. By plastically deforming the blade 80, advantages are gained in obviating the need for a locking arrangement to keep the anchor 58 in place.

Some of the embodiments the anchor 58 may also include additional features and advantages. For example, the anchors 58 shown in FIGS. 66-67 and 70-71 include recesses 118 along the outside surface of the blade 80. These recesses 118 facilitate the bending of the blade 80 during deployment, reducing the amount of force the surgeon needs to apply. It should also be appreciated that some of the anchor embodiments also include different teeth 86 profiles that provide differing levels of engagement with the vertebrae 112, 114.

Referring now to FIGS. 72-77, an embodiment of a lower profile lower profile anchor 120 is illustrated. The lower profile lower profile anchor 120 includes a body 122. The blade portion 124 includes a substantially open center section 126 that extends from the piercing portion 128 back to or through the threaded portion 130. This allows the lower profile anchor 120 to be installed on the screw member 56 with the portion 132 of the body 122 to extend along the surfaces 102, 104, 150 (for surface 15, see for example FIGS. 91-94). Thus, the height of the body 122 may be sized to be substantially equal to or less than the diameter of the screw member 56. This may allow a reduction in the height of the interbody fusion device 50 providing advantages in certain spinal procedures, such as cervical fusion for example.

Referring now to FIGS. 78-82, another anchor 154 is illustrated having three blades 156, 158, 160. Two of the blades 156, 158 are arranged to deploy into the one of the vertebra while the third blade 160 is arranged to deploy into the opposing vertebra. In circumstances where either a longer blade 80 is used or patient anatomy includes narrower vertebrae, this embodiment may provide additional advantages when multiple interbody fusion devices are being implanted in a patient. The arrangement of the blades 156, 158, 160 in this manner allows multiple interbody fusion devices to be implanted, in adjacent levels of vertebrae, without blades from the adjacent devices interfering with each other.

Figure 1:
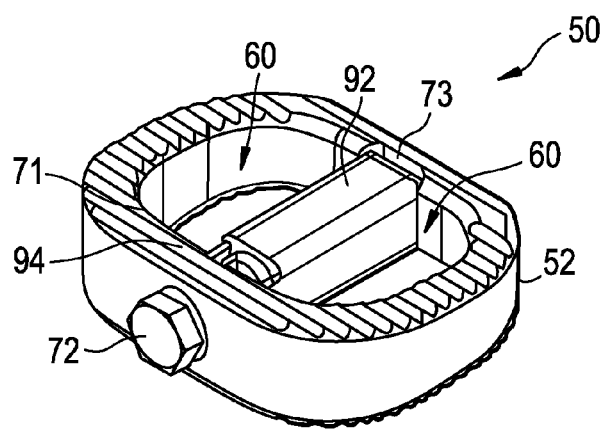
FIGS. 1-4 are an illustration of an interbody fusion device in accordance with an embodiment of the invention.
Figure 2:
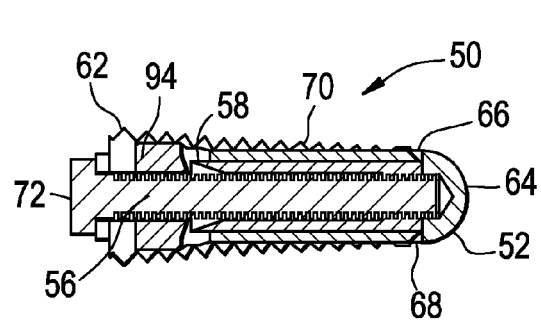
Figure 3:
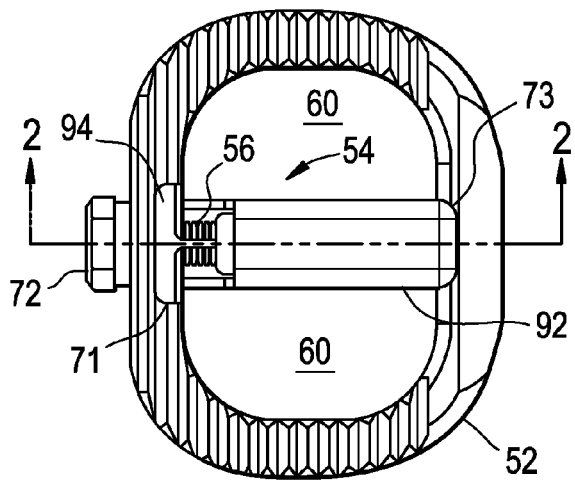
Figure 4:
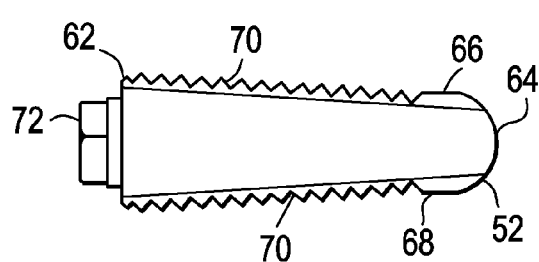
Figure 14:
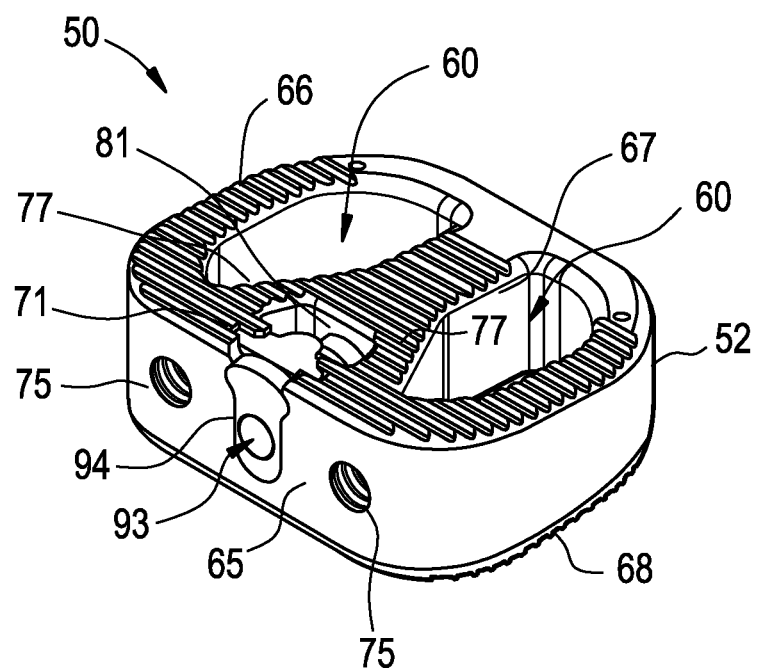
FIGS. 14-17 are an illustration of an interbody fusion device in accordance with another embodiment of the invention.
Figure 15:
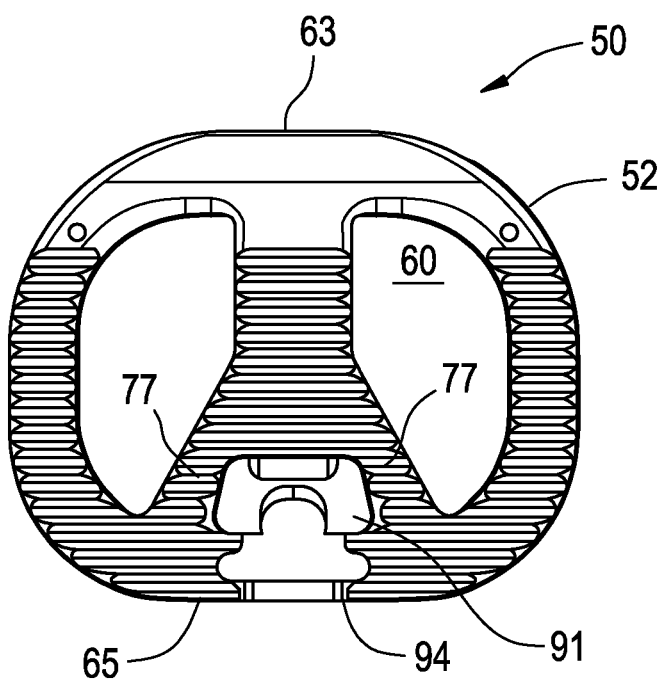
Figure 16:
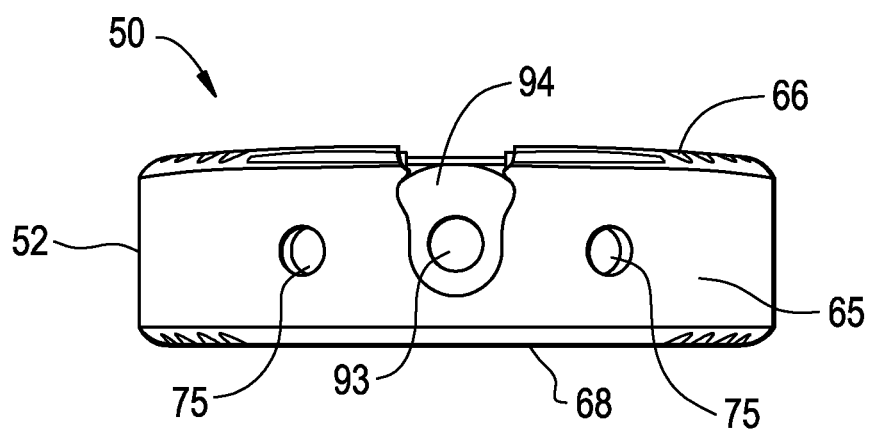
Figure 17:
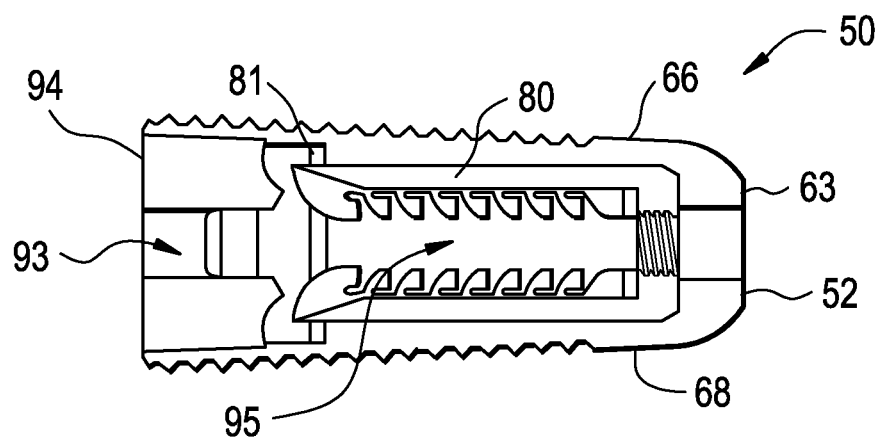
Figure 18:
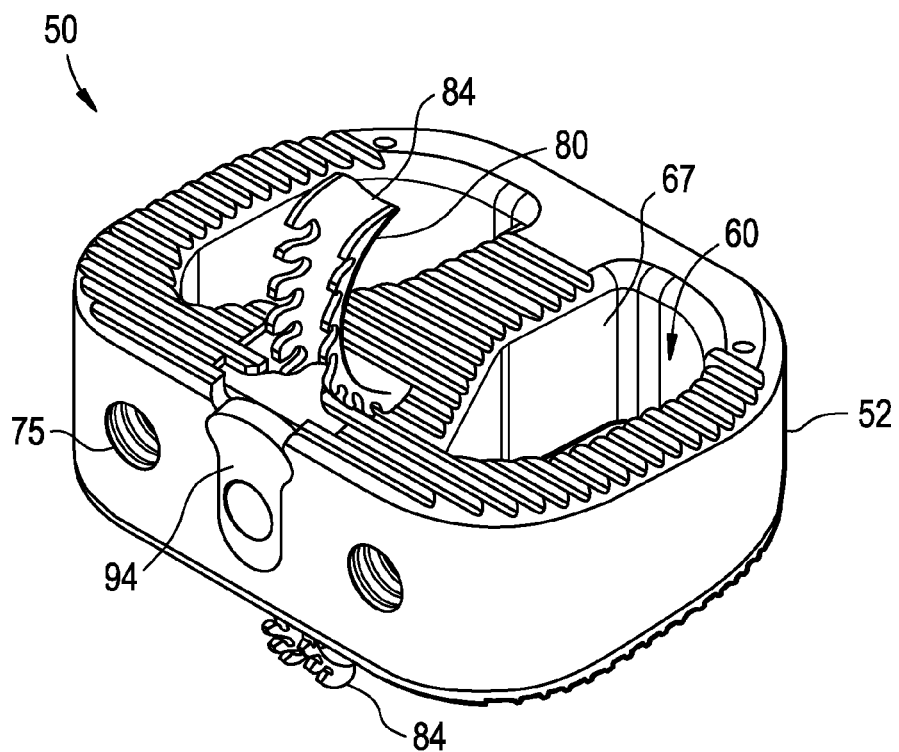
FIGS. 18-19 are an illustration of an interbody fusion device of FIG. 14 in the extended or deployed position.
Figure 41:
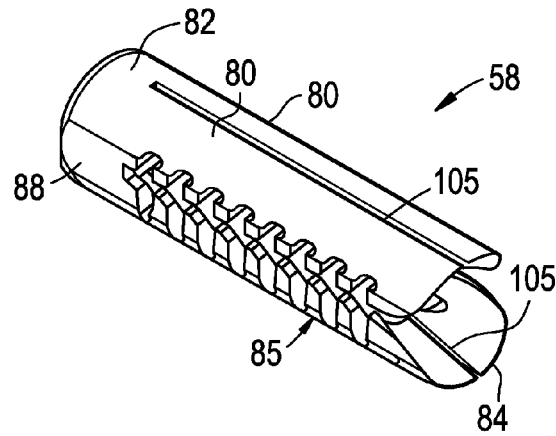
FIGS. 41-43 are an illustration of another embodiment of an anchor having multiple blades for use in the interbody fusion device shown in FIGS. 1-29.
Figure 42:
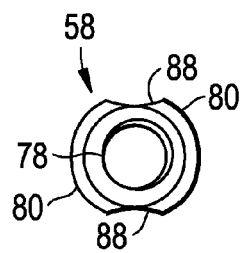
Figure 43:
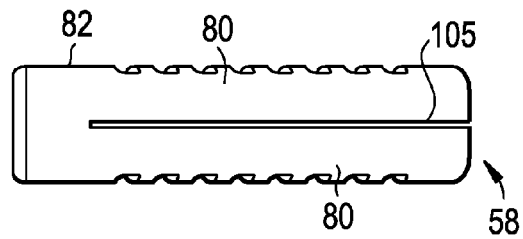
Figure 44:
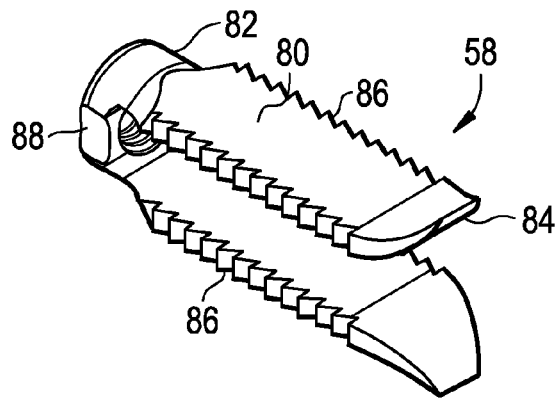
FIGS. 44-46 are an illustration of another embodiment of an anchor for use in the interbody fusion device shown in FIGS. 1-29.
Figure 45:
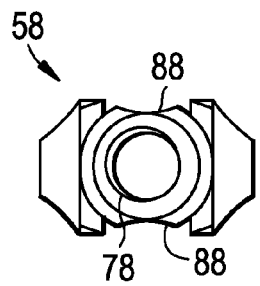
Figure 46:
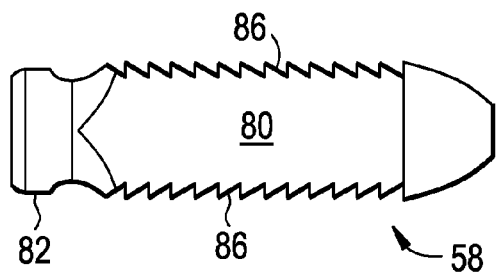
Figure 47:
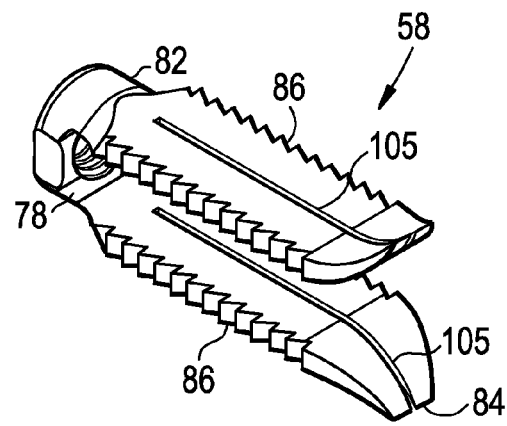
FIGS. 47-49 are an illustration of another embodiment of an anchor having multiple blades for use in the interbody fusion device shown in FIGS. 1-29.
Figure 48:
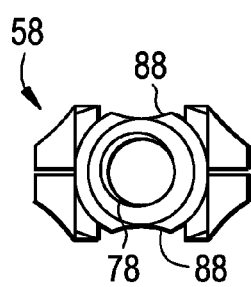
Figure 49:
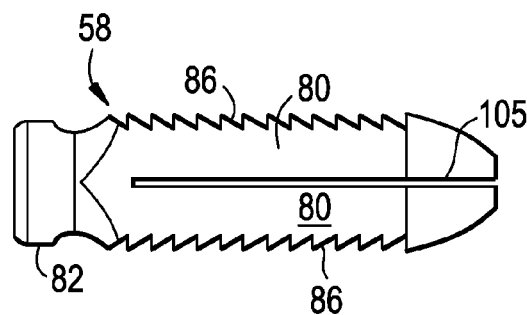
Figure 50:
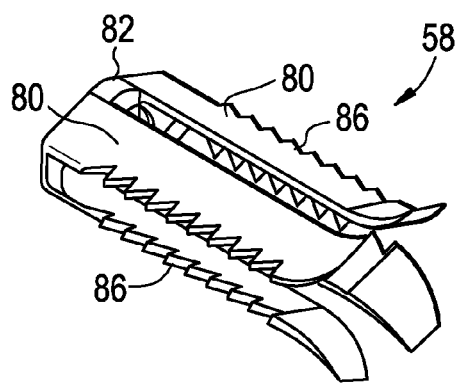
FIGS. 50-54 are an illustration of another embodiment of an anchor having multiple blades for use in the interbody fusion device shown in FIGS. 1-29.
Figure 51:
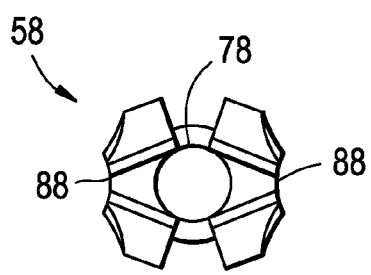
Figure 52:
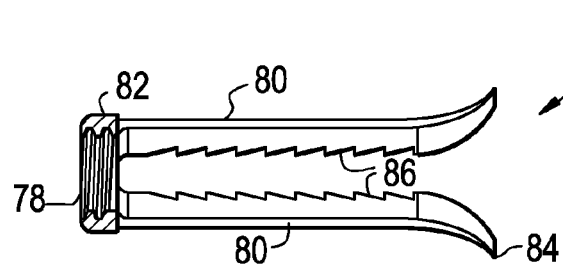
Figure 53:
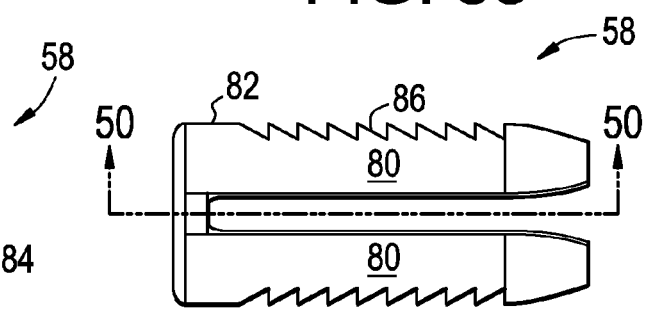
Figure 54:
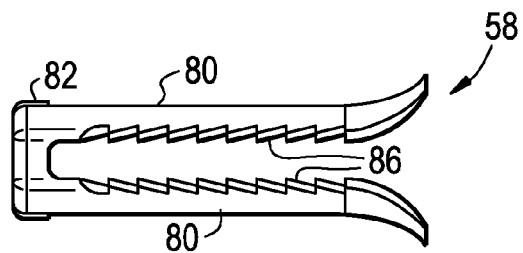
Figure 55:
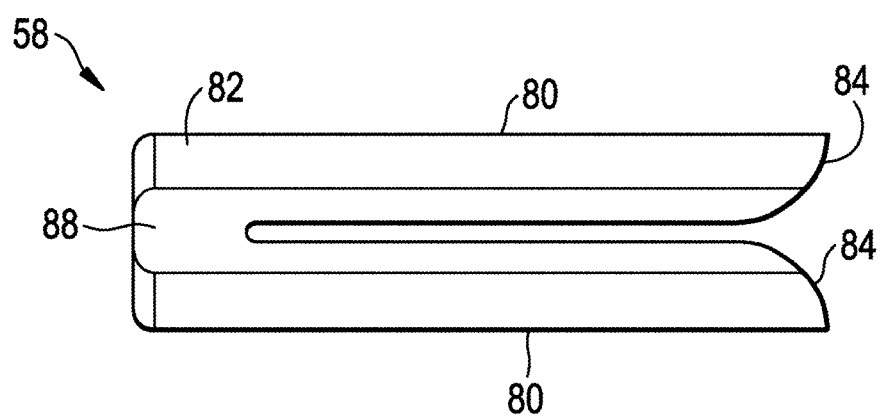
FIGS. 55-56 are an illustration of another embodiment of an anchor having no teeth for use in the interbody fusion device shown in FIGS. 1-29.
Figure 56:
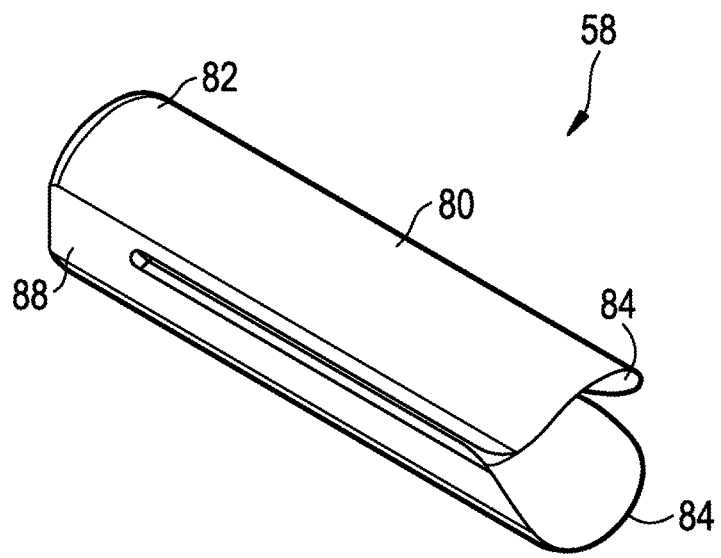
Figure 57:
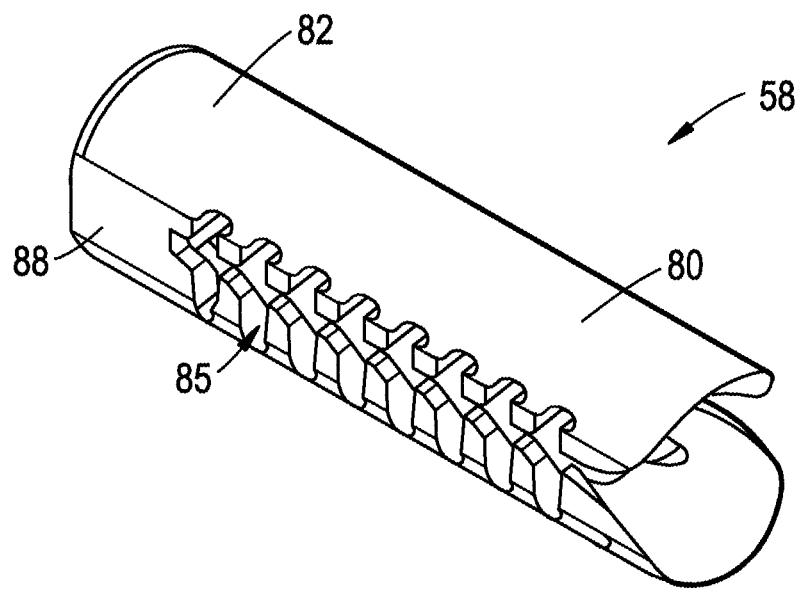
FIGS. 57-61 are an illustration of another embodiment of an anchor used in the interbody fusion device shown in FIGS. 1-29.
Figure 58:
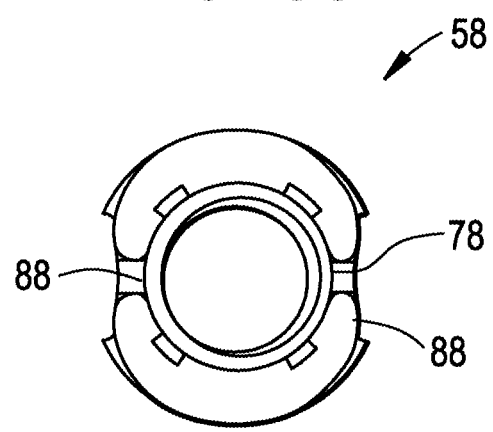
Figure 59:
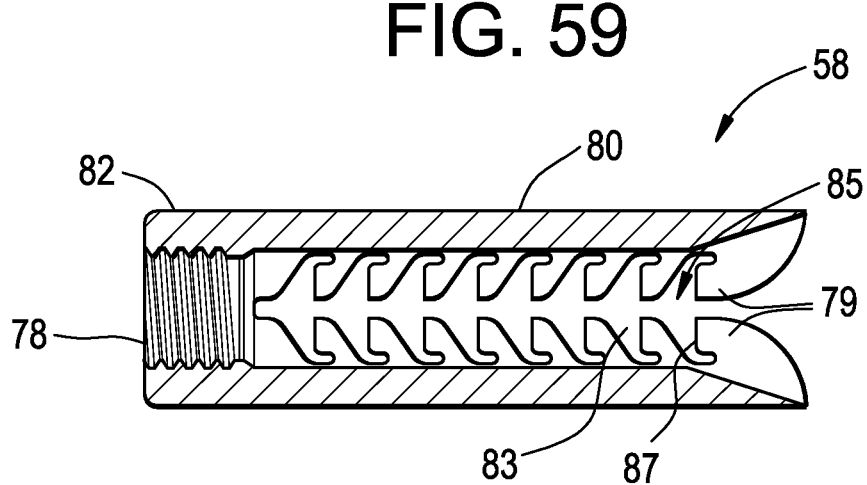
Figure 60:
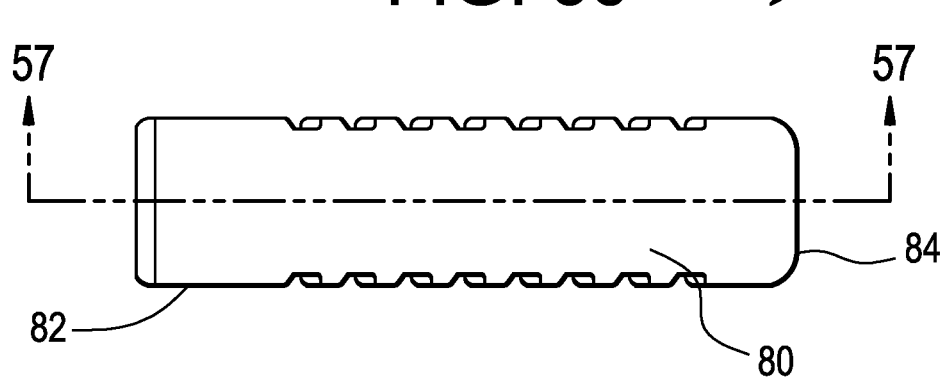
Figure 61:
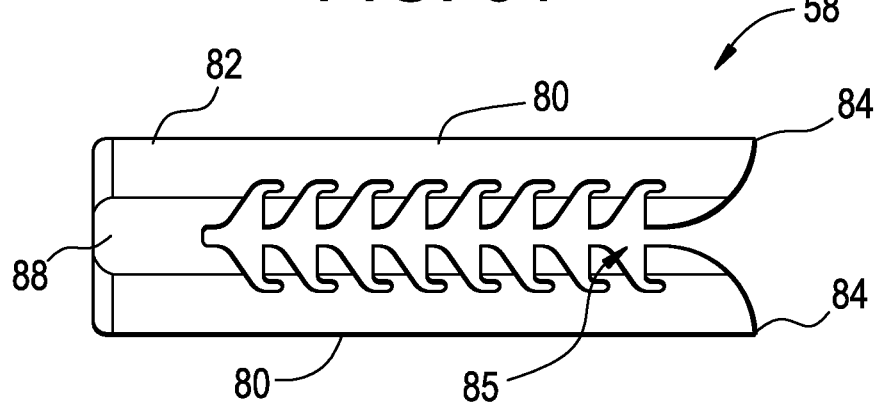
Figure 62:
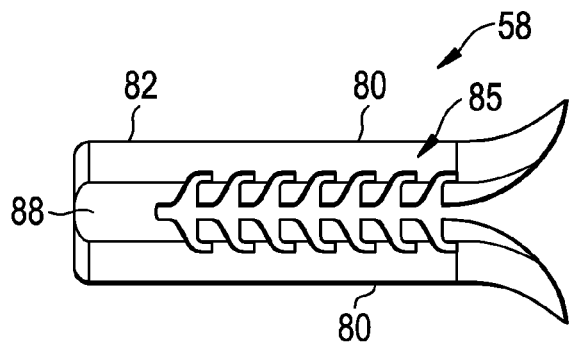
FIGS. 62-63 are an illustration of another embodiment of an anchor for use in the interbody fusion device shown in FIGS. 1-29.
Figure 63:
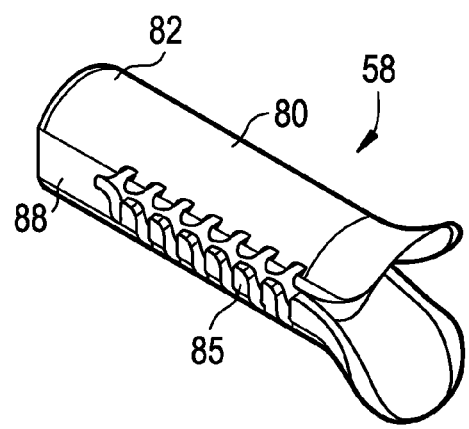
Figure 64:
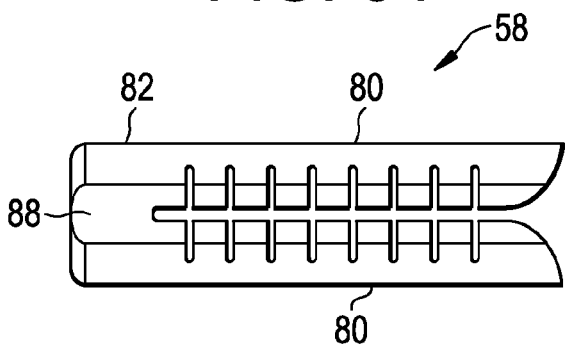
FIGS. 64-65 are an illustration of another embodiment of an anchor for use in the interbody fusion device shown in FIGS. 1-29.
Figure 65:
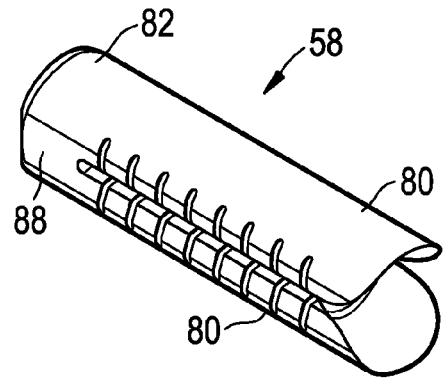
Figure 66:
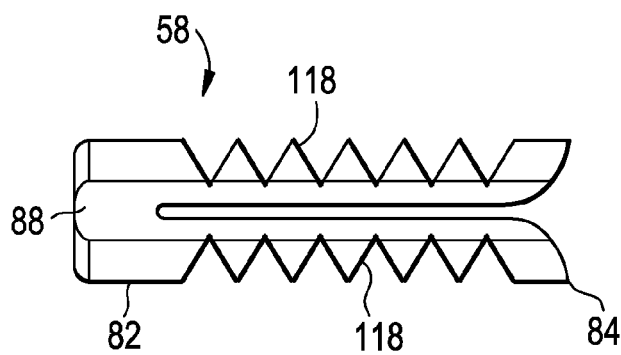
FIGS. 66-67 are an illustration of another embodiment of an anchor for use in the interbody fusion device shown in FIGS. 1-29.
Figure 67:
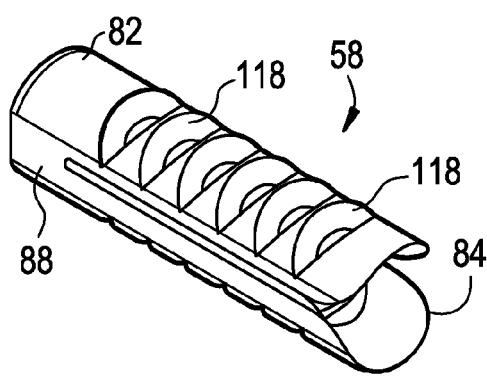
Figure 68:
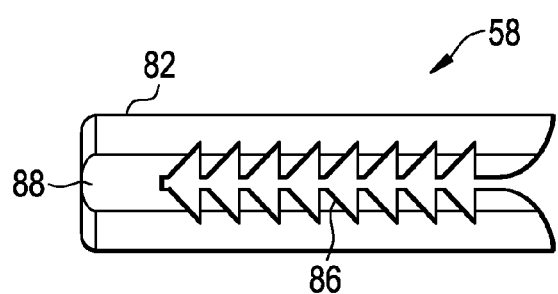
FIGS. 68-69 are an illustration of another embodiment of an anchor for use in the interbody fusion device shown in FIGS. 1-29.
Figure 69:
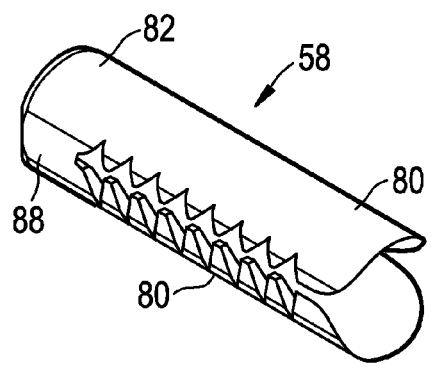
Figure 70:
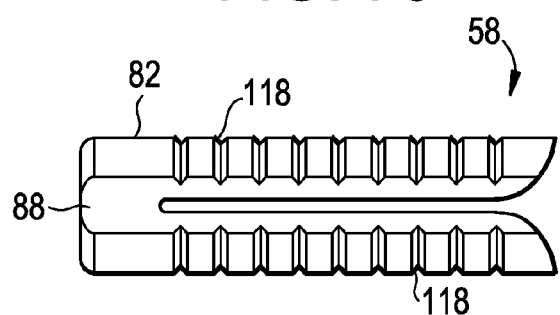
FIGS. 70-71 are an illustration of another embodiment of an anchor for use in the interbody fusion device shown in FIGS. 1-29.
Figure 71:
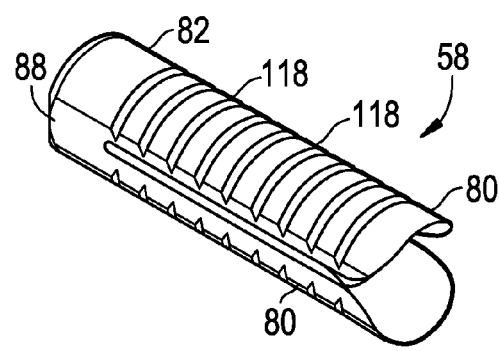
Figure 72:
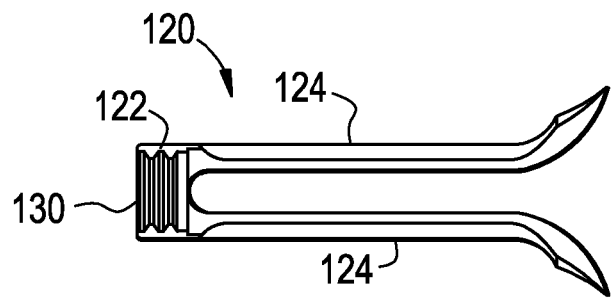
FIGS. 72-76 are an illustration of another embodiment of an anchor having a smaller profile for use with the interbody fusion device shown in FIGS. 1-29.
Figure 73:
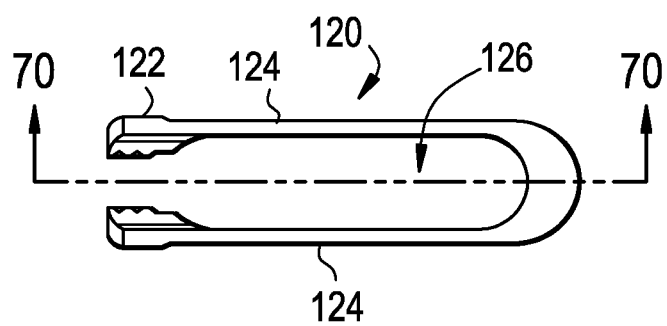
Figure 74:
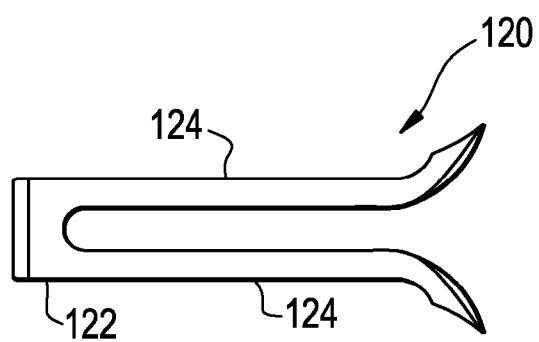
Figure 75:
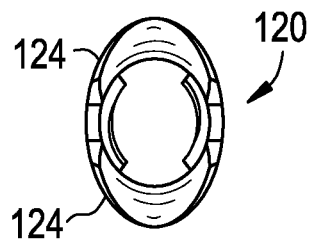
Figure 76:
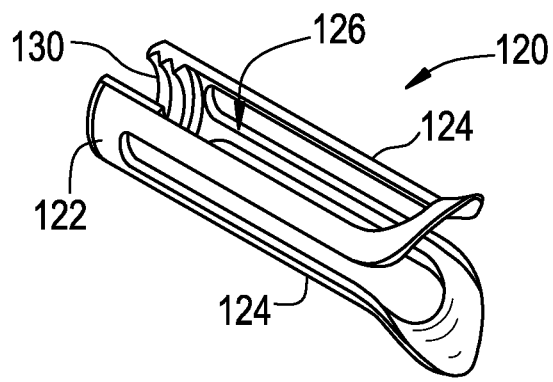
Figure 77:
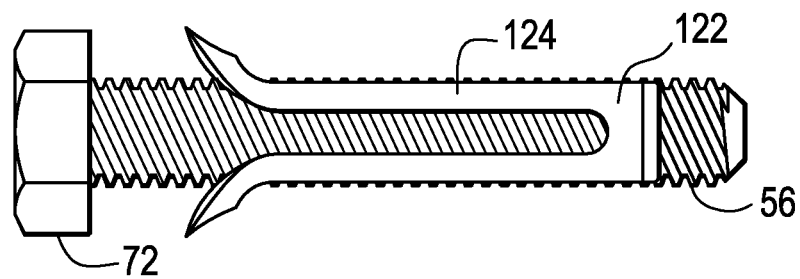
FIG. 77 is an illustration of the anchor of FIGS. 72-76 assembled on an exemplary screw member.
Figure 78:
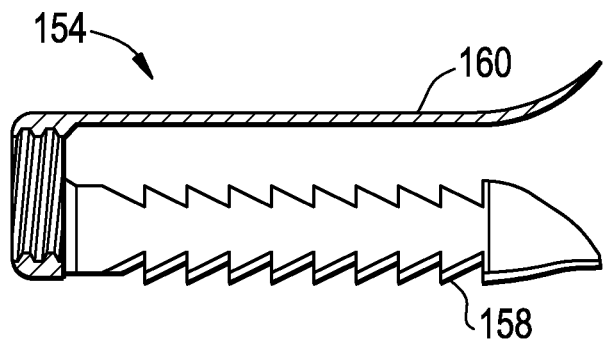
FIG. 78-82 are an illustration of another embodiment of an anchor having multiple blades for use with the interbody fusion device shown in FIGS. 1-29.
Figure 79:
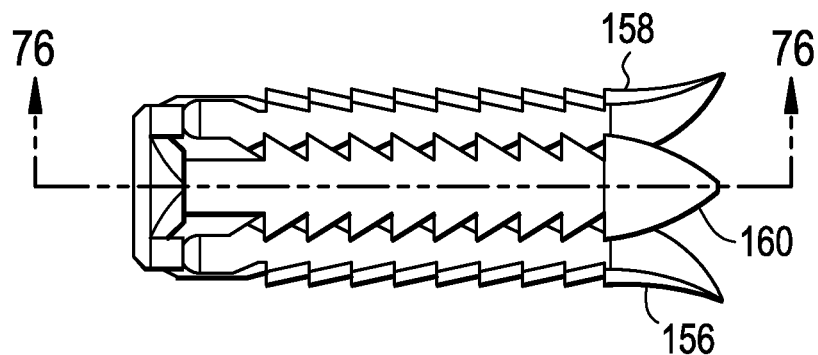
Figure 80:
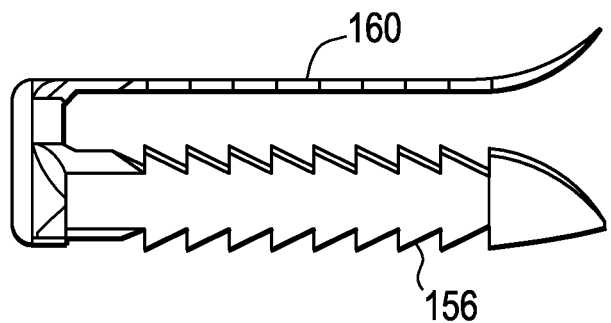
Figure 81:
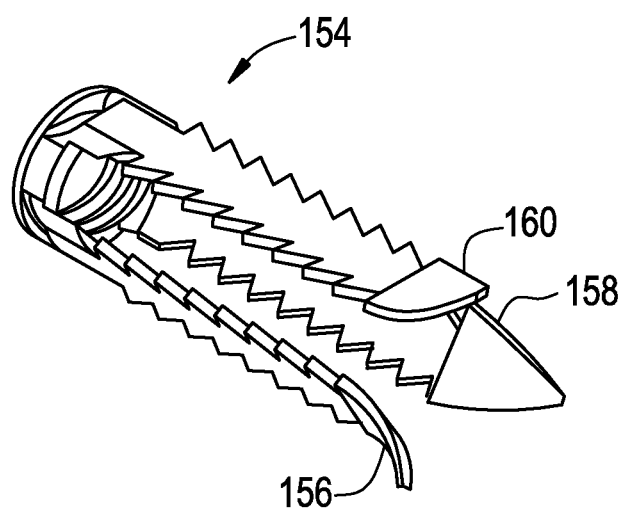
Figure 95:
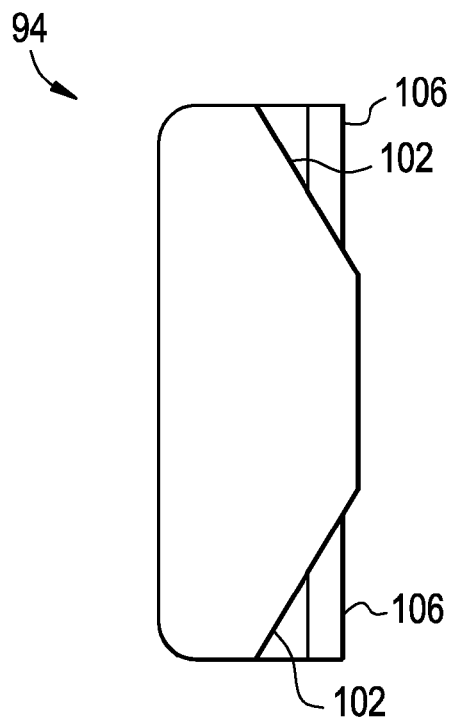
FIGS. 95-96 are an illustration of another embodiment of a ramp member used with an anchor having multiple blades.
Figure 96:
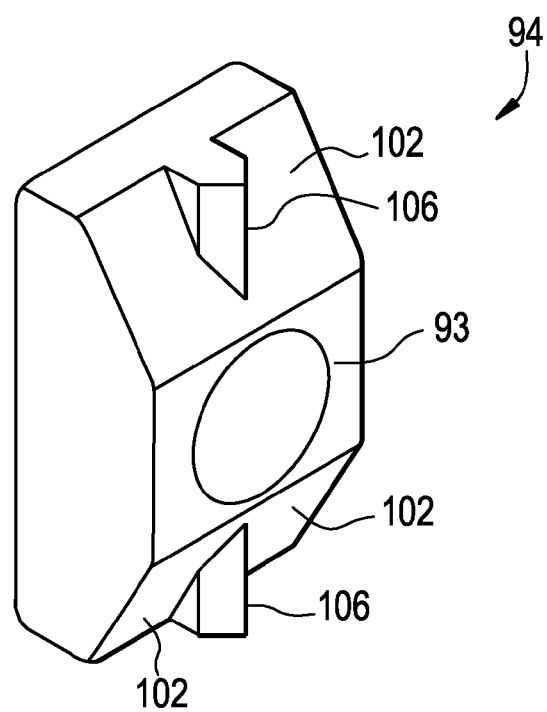

Referring now to FIGS. 83-103, embodiments of the ramp member 94 will be described. It should be appreciated that the ramp member 94 may be coupled to the interbody cage 52 in several ways. The ramp member 94 may be coupled by a snap-fit connection, as illustrated in FIG. 14 for example, or may also be captured on the screw member 56 within the anterior slot 71, as shown in FIG. 2 for example. Other coupling means include, but are not limited to, press fit, bonding or mechanical fasteners. In other embodiments, the ramp member 94 may be incorporated into the surgical tool and therefore removed from the patient at the conclusion of the surgical procedure. The ramp member 94 includes one or more surfaces 102 that cooperate with the blade 80 to urge the piercing portion 84 away from the screw member 56 extending the blade from the contact surfaces 66, 68 and into the vertebrae. In some embodiments, the ramp member 94 may include four surfaces 102, 104 (FIGS. 85-86, 89-90) or a frustoconical surface 150 (FIGS. 91-93), that urge the separation and spreading of the blades 80 on a multi-bladed bladed anchor (FIGS. 41, 47, 50). One embodiment also includes a projection 106 (FIGS. 95-96) that further separates and provides additional deflection of the multiple blades of the anchor. The ramp member 94 may also include a pair of slots 108, 110 that are sized to receive the projections 98 on the guide housing 92. It should be appreciated that the embodiments illustrated in FIGS. 83-103 may also include the slots 108, 110. The surfaces 102, 104 may be a sloped planar surface, an arcuate surface, or have first curvature and a second curvature to form a saddle shaped surface as illustrated in FIGS. 97-100 for example.

For exemplary purposes, the embodiment of the ramp member 94 illustrated in FIGS. 97-100 will be described. In this embodiment, the ramp member 94 includes a body 134 that is sized to fit in the anterior slot 71. A first projection 136 extends from the body 134, in the embodiment of FIG. 14 the first projection 136 extends towards the anterior side 62. The first projection includes a profiled portion 138 that cooperates with a substantially similarly shaped portion of the anterior slot 71 to define a snap-fit connection. The snap-fit defined by the profiled portion 138 retains the ramp member 94 in the anterior slot 71 preventing migration of ramp member 94 during use. Opposite the first projection 136, a second projection 140 extends from the body 134. The second projection includes a pair of surfaces 102 that are arranged to deflect the blade 80 through the opening 91. In the embodiment illustrated in FIGS. 97-100, the surface 102 has first curvature sized and shaped to substantially match the curvature or radius of the blade 80. The surface 102 is also defined by a second curvature sized and shaped to deflect the blade 80 through the opening 91 with the desired exit angle and curvature. The first curvature and the second curvature combine to form a substantially saddle shape. In some embodiments, the first curvature lies substantially in a plane parallel to the longitudinal axis of the body, while the second curvature lies in a transverse plane to the first curvature forming a saddle shape. The ramp member 94 also includes an opening 93 that extends through the first projection 136, the body 134 and the second projection 140. In some embodiments, the opening 93 is large enough to separate the surfaces 102 forming a gap 142 in the second projection 140.

Figure 101:
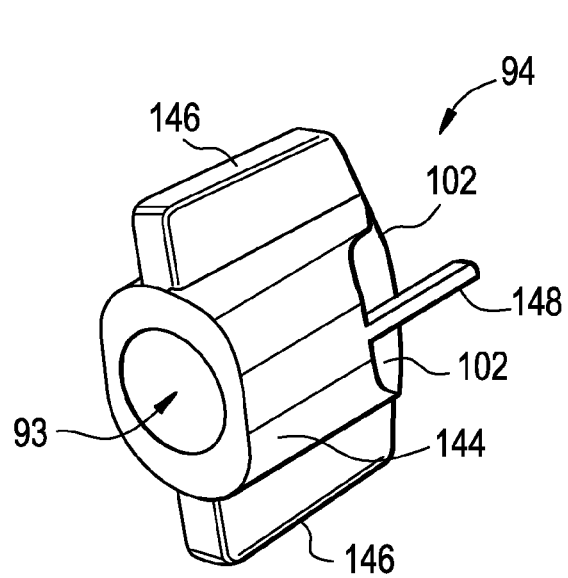
FIGS. 101-103 illustrate another embodiment of a ramp member for use with the interbody fusion device of FIGS. 20-22.
Figure 102:
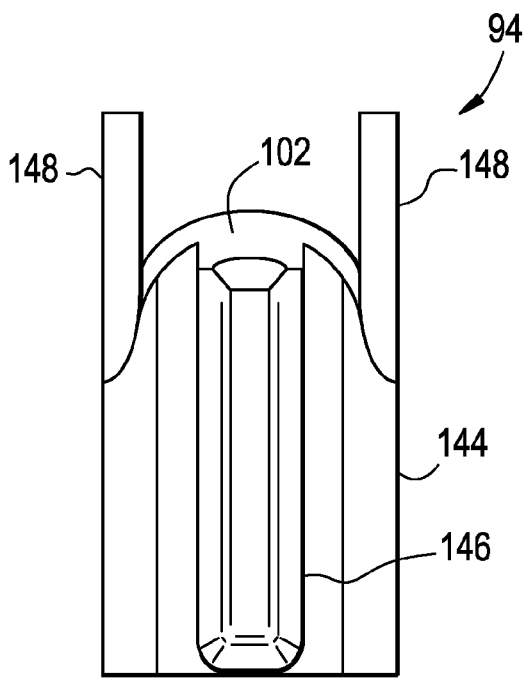
Figure 103:
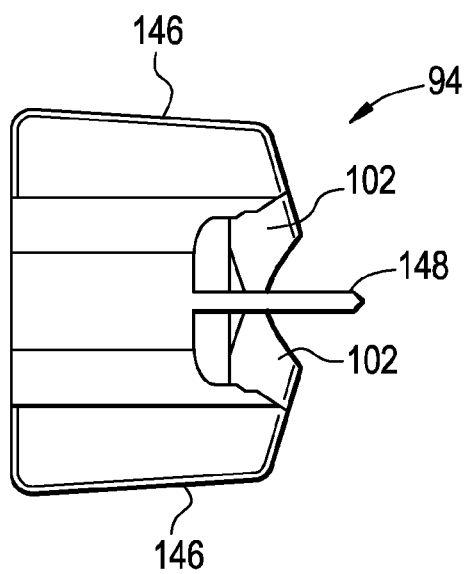
Figure 104:
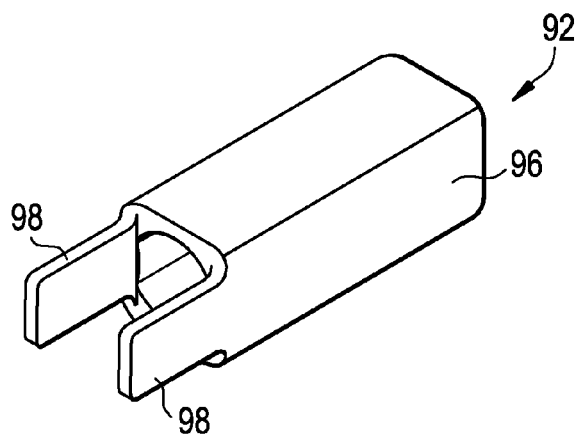
FIGS. 104-107 are an illustration of an exemplary guide housing for use with the interbody fusion devices of FIGS. 1-13.
Figure 105:
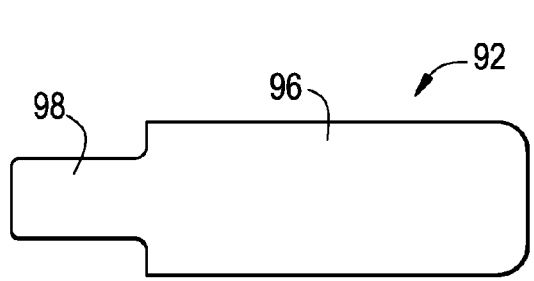
Figure 106:
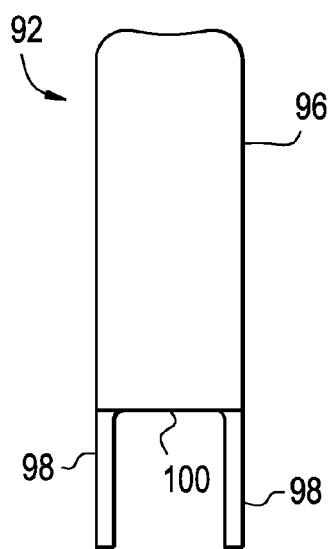
Figure 107:
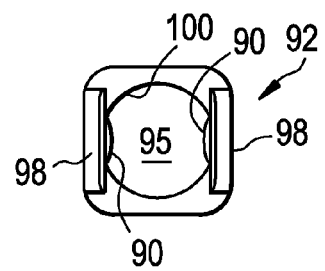
Figure 108:
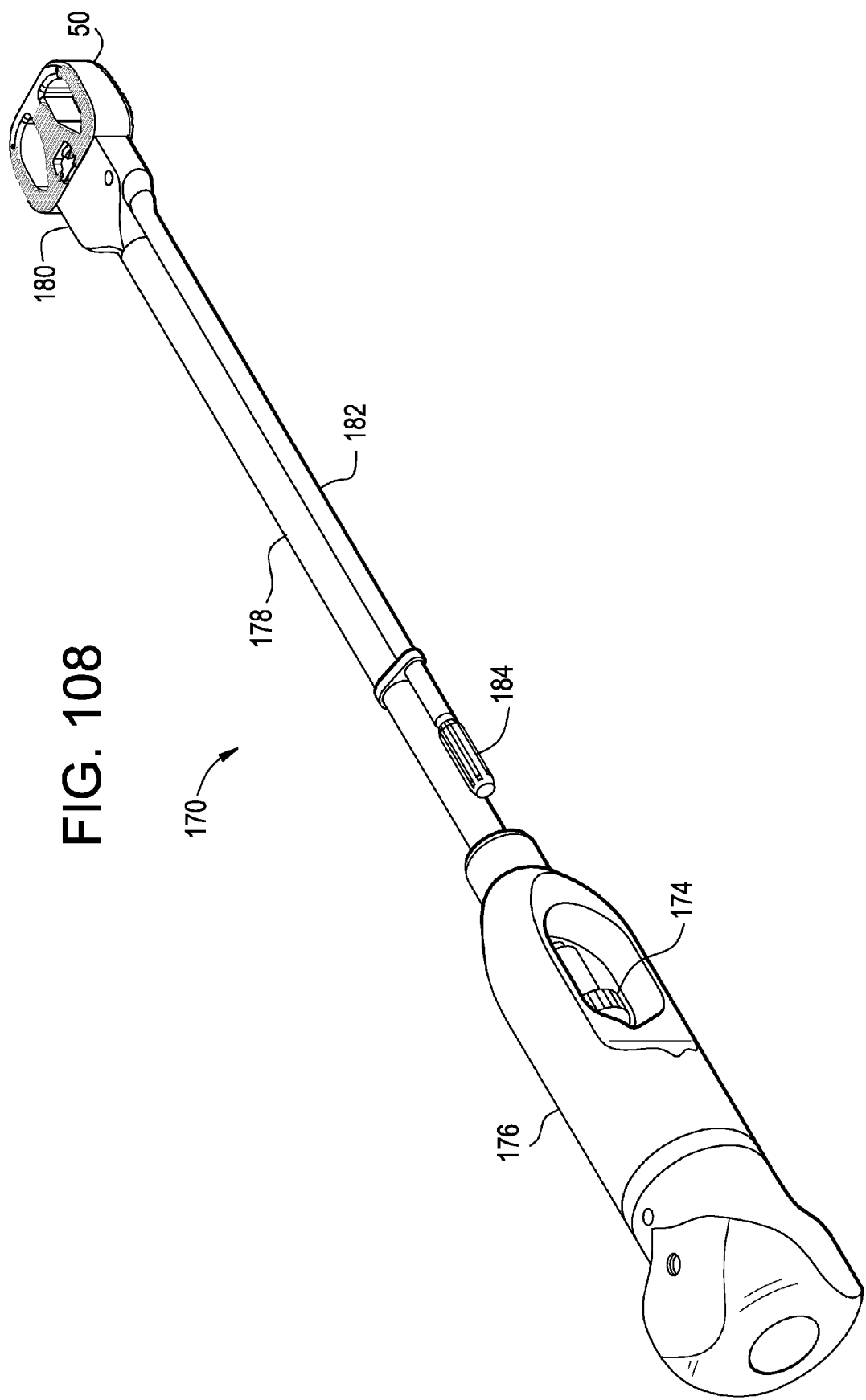
FIGS. 108-111 are an illustration of a surgical tool for use with the interbody fusion device of FIGS. 14-25.
Figure 109:
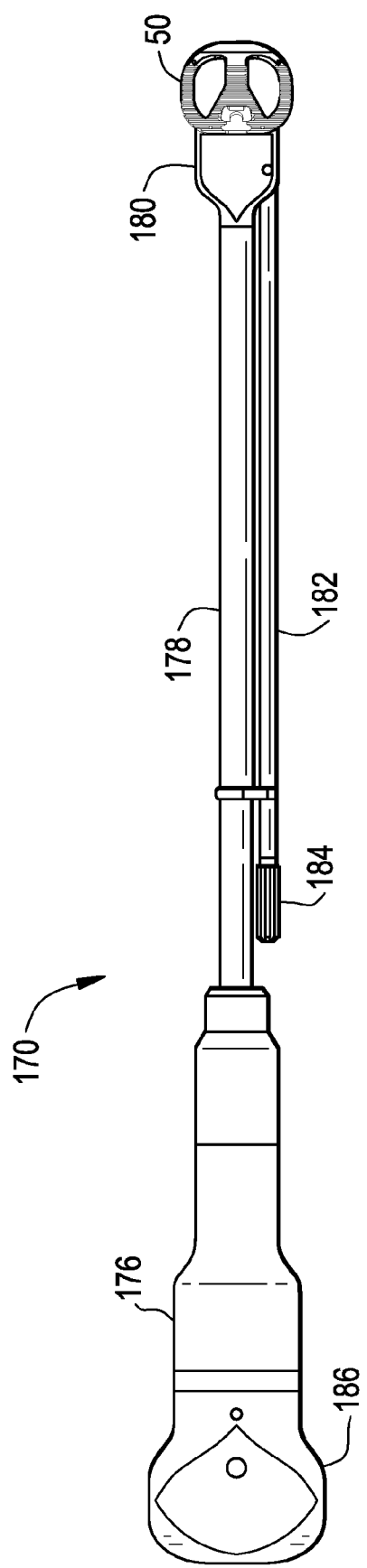
Figure 110:
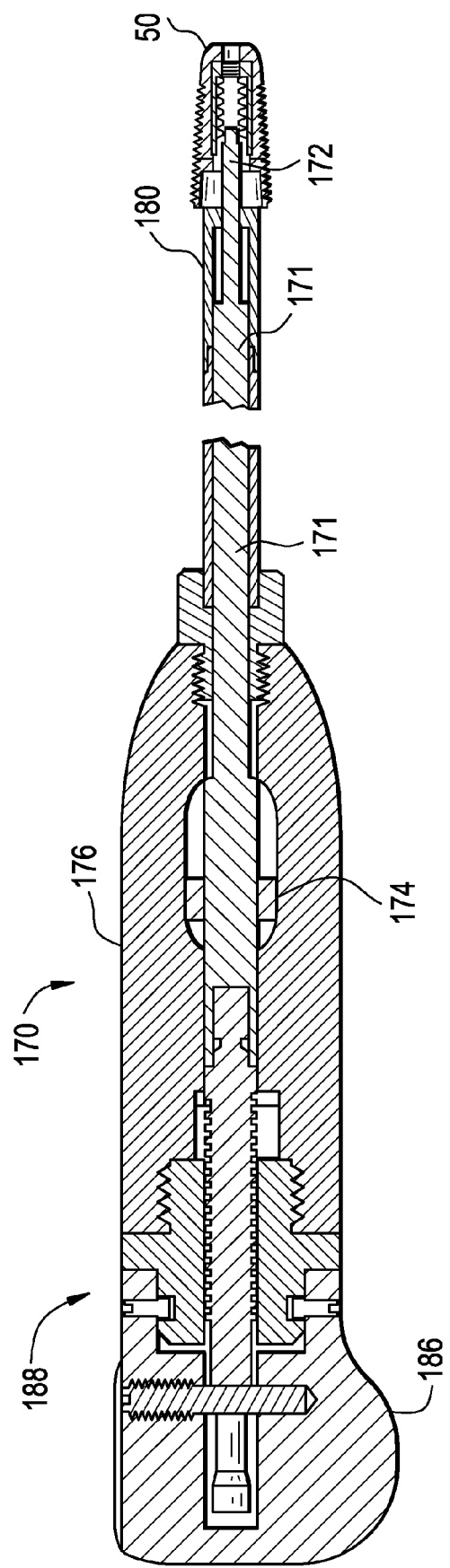

Another exemplary embodiment of the ramp member 94 is illustrated in FIGS. 101-103. This embodiment of ramp member 94 may be used with an interbody cage 52, such as that illustrated in FIG. 20 for example, where the ramp member 94 is inserted axially into the interbody cage 52. In this embodiment, the ramp member 94 includes a body 144 having a central opening 93. A pair of first projections 146 extends from the body 144 and each is sized to be received in the anterior slot 71. On one end of the body 144, a pair of surfaces 102 is formed. In one embodiment, the surfaces 102 extend from the body 144 onto one end of the first projections 146. Extending from the body 144, adjacent the surfaces 102, a pair of second projections 148 extend substantially parallel to the opening 93. The second projections 148 assist the separation of the blades 80 as the anchor 58 is moved.

Referring to FIGS. 108-111, an embodiment of a surgical tool 170 for use with the interbody fusion device 50 is illustrated. The surgical tool 170 includes a handle 176. Extending from one end of the handle 176 is an elongated first shaft 178 with a support member 180 on a distal end. The support member 180 is generally sized and shaped to couple to the interbody fusion device 50. A second shaft 182 is coupled to the first shaft 178. The second shaft 182 includes an actuation portion 184 on an end adjacent the handle 176. Opposite the actuation portion 184, the second shaft 182 includes a threaded portion 192 that extends through the support member 180 and is adapted to couple with the feature 75 in the interbody fusion device 50. It should be appreciated that in embodiments using the screw member 56, the end of the shaft 171 is configured to engage the actuation portion 72 of the screw member 56.

The surgical tool 170 also includes a shaft 171 having a threaded rod 172 that extends from the handle 176 through the support member 180. A knob 174 is coupled to the threaded rod 172 allowing the surgeon to rotate the shaft 171 and couple the end of the threaded rod 172 into the anchor 58. It should be appreciated that once the second shaft 182 is coupled to the feature 75 and the shaft 171 is inserted through the opening in either the interbody cage 52 or the ramp member 94 and coupled to the anchor 58, the interbody fusion device 50 and the surgical tool 170 are securely coupled together.

The surgical tool 170 also includes a second or actuation knob 186 arranged on one end. The actuation knob 186 is coupled to the shaft 171 via a threaded portion 188, as is known in the art, to cause the shaft 171 to move axially within the handle 176 and first shaft 178. As the actuation knob 186 is actuated, the shaft 171 moves the anchor 58 relative to the interbody cage 52. It should be appreciated that the actuation of the actuation knob 186 can be used to cause the anchor to move from the retracted or first position to the extended or second position or vice versa. As will be discussed in more detail below, once the procedure has been completed, the surgeon uses the knob 174 to disengage the shaft 171 from the anchor 58 and the actuation portion 184 to disengage the second shaft 182 from the interbody cage 52.

Figure 111:
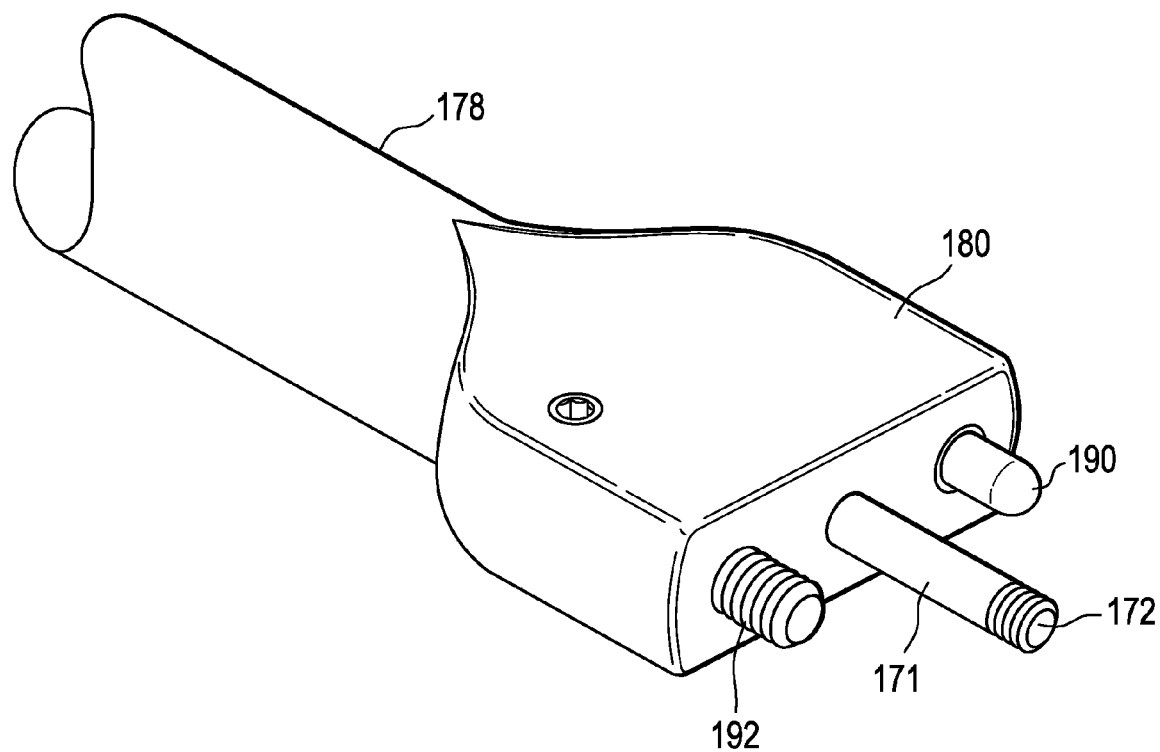

It should be appreciated that in embodiments where the interbody fusion device has a screw member 56, the shaft 171 includes an end adapted to couple with the screw member actuation portion 72. Further, in some embodiments, a third shaft 190 may be coupled to the first shaft 178 opposite the second shaft 182. The third shaft 190 would be arranged to extend through the support member 180 and couple to the feature in the interbody cage 52. The third shaft 190 may be a pin as illustrated in FIG. 111, or have a threaded end similar to the second shaft 182.

It should be appreciated that while this embodiment illustrates a single surgical tool 170, in other embodiments, multiple surgical tools may be used for insertion, deployment, retraction, and/or removal.

During the surgical procedure, the surgeon couples the surgical tool to the interbody fusion device 50 by coupling the second shaft 182 to the feature 75 in interbody fusion cage 52 and inserting the shaft 171 into the interbody fusion device 50. The surgeon rotates knob 174 to rotate shaft 171 and couple the threaded rod 172 to the threaded portion 78 of anchor 58. If desired, the surgeon may also use the optional third shaft 190 to further couple the surgical tool 170 to the interbody fusion device 50.

The surgeon gains access to the intended surgical site and removes the disc material from between the desired superior vertebrae and inferior vertebrae. With the disc material removed, the surgeon uses the surgical tool 170 to guide the interbody fusion device 50 to the intended implantation site. The interbody fusion device 50 is inserted between a superior vertebra 112 and inferior vertebra 114 as shown in FIGS. 112-114. When the surgeon actuates the actuation knob 186, the shaft 171 is moved axially within the surgical tool pulling the anchor 58 from the retracted or first position (e.g. FIGS. 2, 17) towards the extended or second position (e.g. FIGS. 8, 19). It should be appreciated that in embodiments having a screw member 56, the anchor 58 is deployed from its initial position within the guide housing 92 through the rotation of the screw member 56.

As the actuation knob 186 continues to be rotated, the anchor 58 is moved with the blade 80 contacting the ramp member 94. It should be appreciated that the center portion 67 or guide housing 92 keeps the anchor 58 centered within the interbody cage 52 and the features 88/90 provide a means for preventing rotation of the anchor 58. Further, the leading edge 100 of the guide housing 92 cooperates with the ramp member 94 to define a gap. This gap defines both the angle the blade 80 exits the contact surfaces 66, 68, and the deformation or curvature of the blade 80 as the anchor is moved to the final position.

Figure 8:
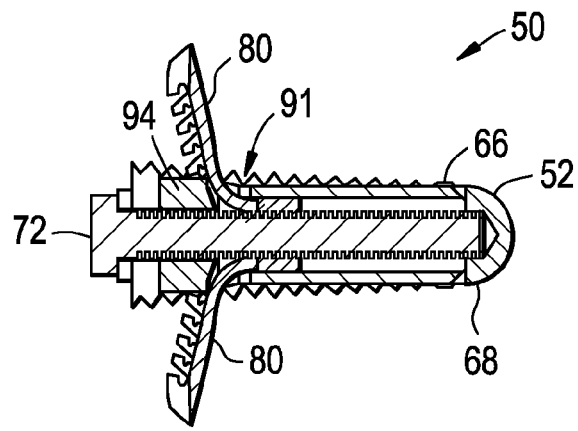
Figure 9:
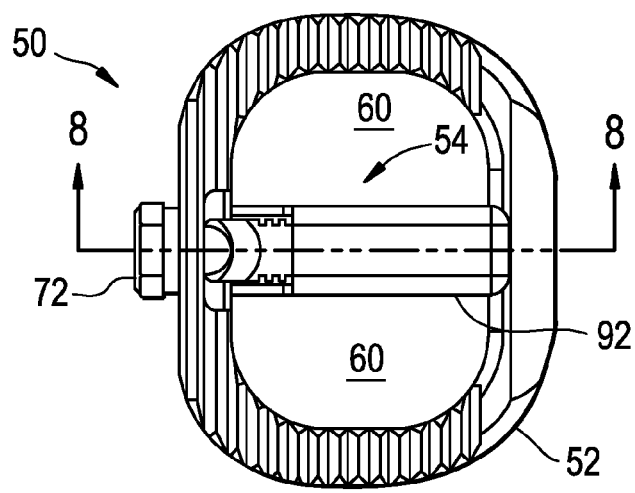
Figure 10:
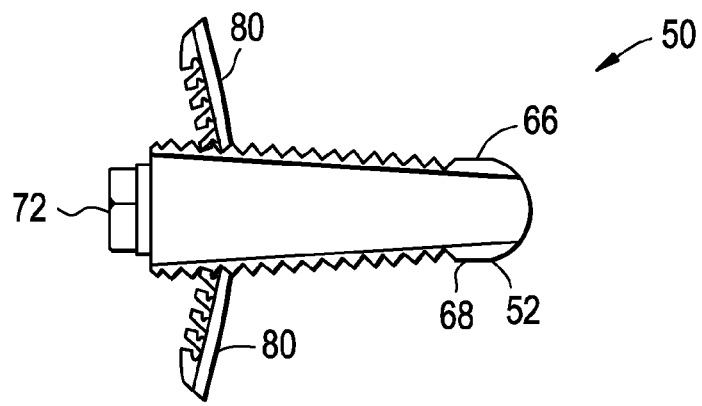
Figure 11:
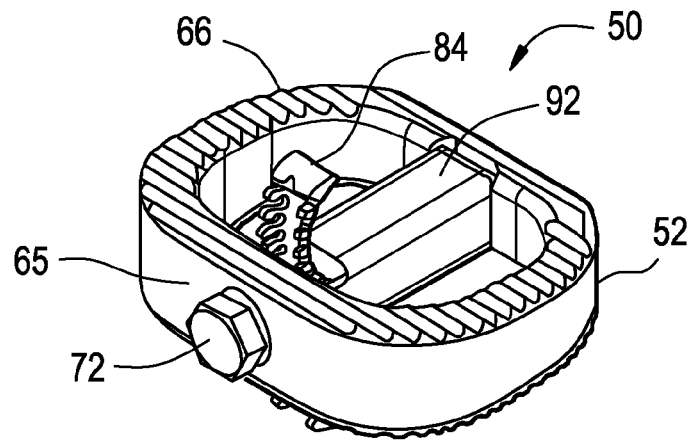
FIGS. 11-13 are an illustration of an interbody fusion device of FIG. 1 with an anchor curved during deployment.
Figure 12:
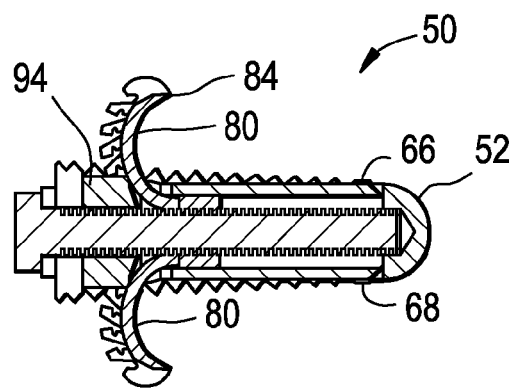
Figure 13:
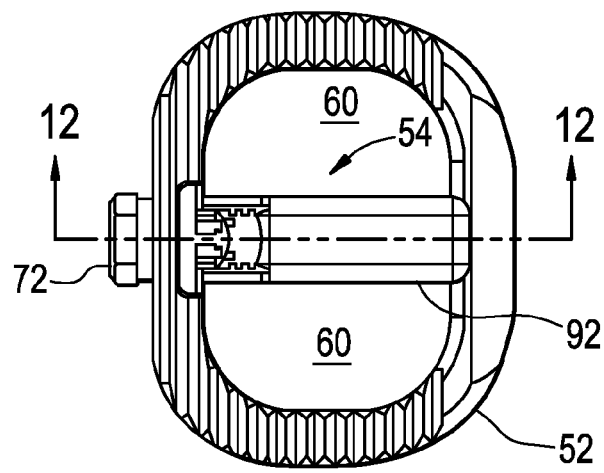

As the actuation knob 186 is rotated, the anchor 58 advances axially and the blade 80 deforms projecting outward by the surface 102 (and in some embodiments surface 104 or surface 150 as well). In the exemplary embodiment, the anchor 58 is advanced toward the anterior side 62. The anchor (s), in whichever embodiment, pierce the cortical shell 116 of the adjacent superior and inferior endplates and extend into the vertebral bodies 112, 114 as shown in FIG. 113. In some embodiments, the blades 80 remain substantially straight while engaging the vertebral bodies 112, 114 (FIG. 8, FIG. 115). In other embodiments, the blade 80 may be arranged to curve while deploying into the vertebral bodies 112, 114 (FIGS. 12, 19). In the embodiments, the curving of blade 80 in a direction opposite the direction of motion of the blade body 82 (e.g. towards the posterior side) may provide additional advantages in securing the interbody fusion device 50 to the vertebral bodies 112, 114 and prevent the anchor 58 from moving. This curving of the blade 80 may also provide further advantages in resisting extension of the vertebrae and in lateral bending. As discussed above, in one embodiment, the blade 80 plastically deforms, meaning the blade 80 material is stressed beyond the elastic limit. The plastic deformation of the blade 80 provides advantages in reducing or eliminating a locking member.

Once the anchor 58 is moved to the extended or final position, the surgeon rotates the knob 174 in the opposite direction causing the threaded rod 172 to disengage from the threaded portion 78 of the anchor. Once the shaft 171 is decoupled from the anchor 58, the surgeon rotates the actuation portion 184 to disengage the second shaft 182 from the interbody cage 52. With the surgical tool 170 decoupled from the interbody fusion device 50, the surgeon can remove the surgical tool from the patient.

In some circumstances it may be desirable for the surgeon to remove, or reposition the interbody fusion device 50. For example, there may be complications in an unrelated part of the surgery, or the surgeon may want to reposition the interbody fusion device 50 to provide better support. One advantage of the interbody fusion device 50 is that the surgeon may utilize the surgical tool 170 in reverse to retract the anchor 58 and the blades 80 into the interbody cage 52. To accomplish this, the surgeon attaches the surgical tool to the interbody fusion device 50 via the second shaft 182 and the shaft 171 to the opening 74 and the anchor threaded portion 78 respectively. The actuation knob 186 is then rotated causing the shaft 171 to slide axially away from the actuation knob 186 and pushing on the anchor 58. As the shaft 171 pushes on the anchor 58, the anchor slides causing the blades 80 to retract into the center bore 95. Once the blades 80 are retracted, the surgeon may remove or reposition the interbody fusion device 50 as desired. It should be appreciated that in embodiment utilizing the screw member 56, the blades 80 are retracted in a similar manner by rotating the screw member 56 in the opposite direction.

The interbody fusion device 50 provides advantages that include the rigid fixation of the stand-alone implant. The interbody fusion device 50 provides additional advantages in resisting motion typically seen in the spinal column such as lateral bending, torsion and extension. The rigidity afforded by this interbody fusion device 50 fixes the adjacent superior and inferior vertebral bodies together allowing for a fusion to occur across the spinal segment. The interbody fusion device 50 provides additional advantages in that the anchor may be moved in both directions to allow deployment, removal, or repositioning. The interbody fusion device 50 also provides advantages in that a single surgical tool may be used to insert, deploy, and remove the implant. The interbody fusion device 50 provides further advantages in that it may be used from an anterior, a lateral or a posterior direction. In some embodiments, the interbody fusion device 50 provides yet further advantages in that the blades are deployed towards the anterior side of the patient and away from the spinal cord.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. An interbody fusion device comprising:
   a cage having a first contact surface and a second contact surface opposite said first contact surface;
   a ramp fixedly coupled to said cage, said ramp having a curved surface thereon; and
   an anchor having a body movably coupled within said cage, said body being linearly movable between a first position and a second position, wherein said first position and said second position are positioned within said cage, said anchor having at least one blade extending from said body and having an end adjacent said ramp, wherein said at least one blade cooperates with said curved surface to direct said at least one blade from said first contact surface when said body moves from said first position to said second position, wherein a curvature of said at least one blade is curved in a direction toward said first position when said body is in said second position;
   wherein said at least one blade includes at least one slot;
   wherein said at least one blade includes a pair of opposing semi-circular surfaces and a pair of opposing sides between said end and said body and transverse to said pair of opposing surfaces, wherein at least one of said opposing sides includes an edge, said at least one slot being positioned on said edge.

2. An interbody fusion device for implanting between vertebrae, said vertebrae having an anterior side and a posterior side, said interbody fusion device comprising:
   a cage having a first contact surface and a second contact surface, an anterior wall between said first contact surface and said second contact surface, a ramp portion having a curved surface arranged adjacent said anterior wall, and a first opening between said first contact surface and said second contact surface adjacent said ramp portion;
   an anchor slidably coupled within said cage and having an end and at least one blade extending from the end, wherein said end is linearly movable between a first position towards said anterior wall to a second position, wherein said first position and said second position are arranged within said cage, wherein said at least one blade cooperates with said curved surface to move through said first opening when said end moves from said first position to said second position, wherein said at least one blade is curved in a direction toward said first position when in said second position
   wherein said at least one blade includes at least one slot;
   wherein said at least one blade includes a pair of opposing semi-circular surfaces and a pair of opposing sides between said end and said body and transverse to said pair of opposing surfaces, wherein at least one of said opposing sides includes an edge, said at least one slot being positioned on said edge.

3. The interbody fusion device of claim 2 wherein said cage includes a second opening transverse to said anterior wall adjacent said ramp portion, said anchor being arranged in said second opening.

4. The interbody fusion device of claim 3 wherein:
said cage further includes a slot extending from said first contact surface into said anterior wall; and,
said ramp portion is coupled to said cage in said slot.

5. The interbody fusion device of claim 3 wherein said blade plastically deforms as said end moves from said first position to said second position.

6. The interbody fusion device of claim 2 wherein said at least slot includes:
a plurality of slots along said edge.

7. The interbody fusion device of claim 6 wherein each of said plurality of slots includes an engagement surface extending from said edge and a relief portion adjacent said engagement surface.

8. The interbody fusion device of claim 2 wherein said end is further arranged to move from said second position to said first position.

9. The interbody fusion device of claim 8 wherein:
said cage includes a third opening in said anterior wall adjacent said ramp portion, said anchor being arranged in said third opening; and,
a member arranged in said third opening, said member engaging said anchor wherein said member is configured to move said anchor.

10. An interbody fusion device comprising:
a cage comprising:
a pair of opposing contact surfaces,
a wall on one end of said cage arranged between said contact surfaces,
a center portion disposed adjacent said wall,
a first opening extending through said contact surfaces between said center portion and said wall,
a second opening arranged in said wall, and,
a third opening in said center portion; and,
an actuator rotationally coupled to the cage;
a ramp member fixedly coupled to said cage, said ramp having a curved surface thereon; and
an anchor slidably arranged in said third opening, said anchor having a body and at least one blade, said body being linearly movable between a first position within said cage, to a second position in response to rotation of the actuator, wherein said first position and said second position are positioned within said cage, and wherein said at least one blade cooperates with said curved surface and extends through said first opening in said second position, wherein said at least one blade is substantially straight in the first position and is curved towards said first position when in said second position;
wherein said at least one blade includes at least one slot;
wherein said at least one blade includes a pair of opposing semi-circular surfaces and a pair of opposing sides between said end and said body and transverse to said pair of opposing surfaces, wherein at least one of said opposing sides includes an edge, said at least one slot being positioned on said edge.

11. The interbody fusion device of claim 10 wherein:
said wall includes a slot; and,
said ramp member is coupled in said slot.

12. The interbody fusion device of claim 10 wherein said ramp member includes a fourth opening.

13. The interbody fusion device of claim 12 further comprising a member arranged in said fourth opening and coupled to said anchor, wherein said member is configured to move said anchor between said first position and said second position.

14. The interbody fusion device of claim 10 wherein said center portion is formed from a guide housing coupled to said cage.

* * * * *